United States Patent
Fried et al.

(10) Patent No.: US 12,003,120 B2
(45) Date of Patent: Jun. 4, 2024

(54) IMPLANT LOCATION DETECTION AND ADAPTIVE TEMPERATURE CONTROL

(71) Applicant: Medtronic, Inc., Minneapolis, MN (US)

(72) Inventors: Andrew Thomas Fried, St. Paul, MN (US); Douglas W. Brown, Shakopee, MN (US); Charles M. Nowell, Longwood, FL (US); Robert J. Monson, St. Paul, MN (US); Venkat R. Gaddam, Plymouth, MN (US); Brett Otteson, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 18/330,152

(22) Filed: Jun. 6, 2023

(65) Prior Publication Data

US 2023/0352988 A1   Nov. 2, 2023

Related U.S. Application Data

(63) Continuation of application No. 17/652,248, filed on Feb. 23, 2022, now Pat. No. 11,705,763.
(Continued)

(51) Int. Cl.
*H02J 50/80* (2016.01)
*A61N 1/378* (2006.01)
(Continued)

(52) U.S. Cl.
CPC .......... *H02J 50/80* (2016.02); *A61N 1/3787* (2013.01); *H02J 7/0047* (2013.01); *H02J 7/02* (2013.01); *H02J 50/10* (2016.02)

(58) Field of Classification Search
CPC .......... H02J 50/80; H02J 50/10; H02J 7/0047; H02J 7/02; A61N 1/3787
(Continued)

(56) References Cited

U.S. PATENT DOCUMENTS

| | | |
|---|---|---|
| 5,897,576 A | 4/1999 | Olson et al. |
| 6,431,748 B1 | 8/2002 | Baratta |

(Continued)

FOREIGN PATENT DOCUMENTS

| | | |
|---|---|---|
| WO | 2013158238 A2 | 10/2013 |
| WO | 2016172530 A1 | 10/2016 |
| WO | 2017053067 A1 | 3/2017 |

OTHER PUBLICATIONS

Notice of Allowance from U.S. Appl. No. 17/652,248 dated Mar. 2, 2023, 10 pp.

*Primary Examiner* — Alfonso Perez Borroto
(74) *Attorney, Agent, or Firm* — Shumaker & Sieffert, P.A.

(57) ABSTRACT

Devices, systems, and techniques are described to detect when a power transmitting and receiving system is in an inefficient position, which may cause a thermal response that less desirable than a more efficient position. The system may power transmitting device configured to wirelessly transfer electromagnetic energy to a power receiving device. Processing circuitry of the system may compute a target output power deliverable by the power transmitting device for a first duration and control the power transmitting device to output the target output power based in part on a heat limit. The processing circuitry may further calculate an energy transfer efficiency to the power receiving unit, update an adjustment factor based on the calculated energy transfer efficiency, and apply the adjustment factor to the heat limit for a subsequent duration.

20 Claims, 13 Drawing Sheets

Related U.S. Application Data

(60) Provisional application No. 63/152,986, filed on Feb. 24, 2021.

(51) Int. Cl.
  *H02J 7/00* (2006.01)
  *H02J 7/02* (2016.01)
  *H02J 50/10* (2016.01)

(58) Field of Classification Search
  USPC .......................................................... 307/104
  See application file for complete search history.

(56) References Cited

U.S. PATENT DOCUMENTS

| | | | |
|---|---|---|---|
| 6,681,135 B1 | 1/2004 | Davis et al. | |
| 7,167,756 B1 | 1/2007 | Torgerson et al. | |
| 7,952,322 B2 | 5/2011 | Partovi et al. | |
| 8,244,367 B2 | 8/2012 | Wahlstrand et al. | |
| 8,335,569 B2 | 12/2012 | Aghassian | |
| 8,496,646 B2 | 7/2013 | Kamen | |
| 8,554,322 B2 | 10/2013 | Olson | |
| 8,784,364 B2 | 7/2014 | Kamen | |
| 8,901,878 B2 | 12/2014 | Prutchi et al. | |
| 9,176,163 B2 | 11/2015 | Heath | |
| 9,209,634 B2 | 12/2015 | Cottrill et al. | |
| 9,225,190 B2 | 12/2015 | Labbe | |
| 9,270,134 B2 | 2/2016 | Gaddam et al. | |
| 9,653,935 B2 | 5/2017 | Cong et al. | |
| 9,851,372 B2 | 12/2017 | Heath et al. | |
| 9,929,584 B2 | 3/2018 | Aghassian et al. | |
| 10,554,069 B2 | 2/2020 | Paralikar et al. | |
| 10,971,943 B2 | 4/2021 | Paralikar et al. | |
| 11,705,763 B2 * | 7/2023 | Fried | A61N 1/3787 307/104 |
| 2003/0050557 A1 | 3/2003 | Susil et al. | |
| 2006/0247738 A1 * | 11/2006 | Schmeling | A61N 1/3787 607/33 |
| 2007/0129767 A1 * | 6/2007 | Wahlstrand | H02J 50/402 607/33 |
| 2007/0167997 A1 * | 7/2007 | Forsberg | A61N 1/3787 607/61 |
| 2008/0272742 A1 | 11/2008 | Hart et al. | |
| 2009/0112291 A1 * | 4/2009 | Wahlstrand | A61N 1/3787 607/61 |
| 2009/0276014 A1 | 11/2009 | Morgan et al. | |
| 2010/0217360 A1 | 8/2010 | Henriksson | |
| 2010/0234921 A1 | 9/2010 | Torgerson et al. | |
| 2010/0256710 A1 | 10/2010 | Dinsmoor et al. | |
| 2011/0077720 A1 | 3/2011 | Torgerson et al. | |
| 2013/0193914 A1 | 8/2013 | Gaddam et al. | |
| 2013/0278226 A1 | 10/2013 | Cong et al. | |
| 2014/0048174 A1 | 2/2014 | Lanigan | |
| 2015/0157869 A1 | 6/2015 | Torgerson et al. | |
| 2016/0187272 A1 | 6/2016 | Ishii et al. | |
| 2019/0190296 A1 | 6/2019 | Paralikar et al. | |
| 2019/0358395 A1 | 11/2019 | Olson et al. | |
| 2022/0134116 A1 | 5/2022 | Fried et al. | |

* cited by examiner

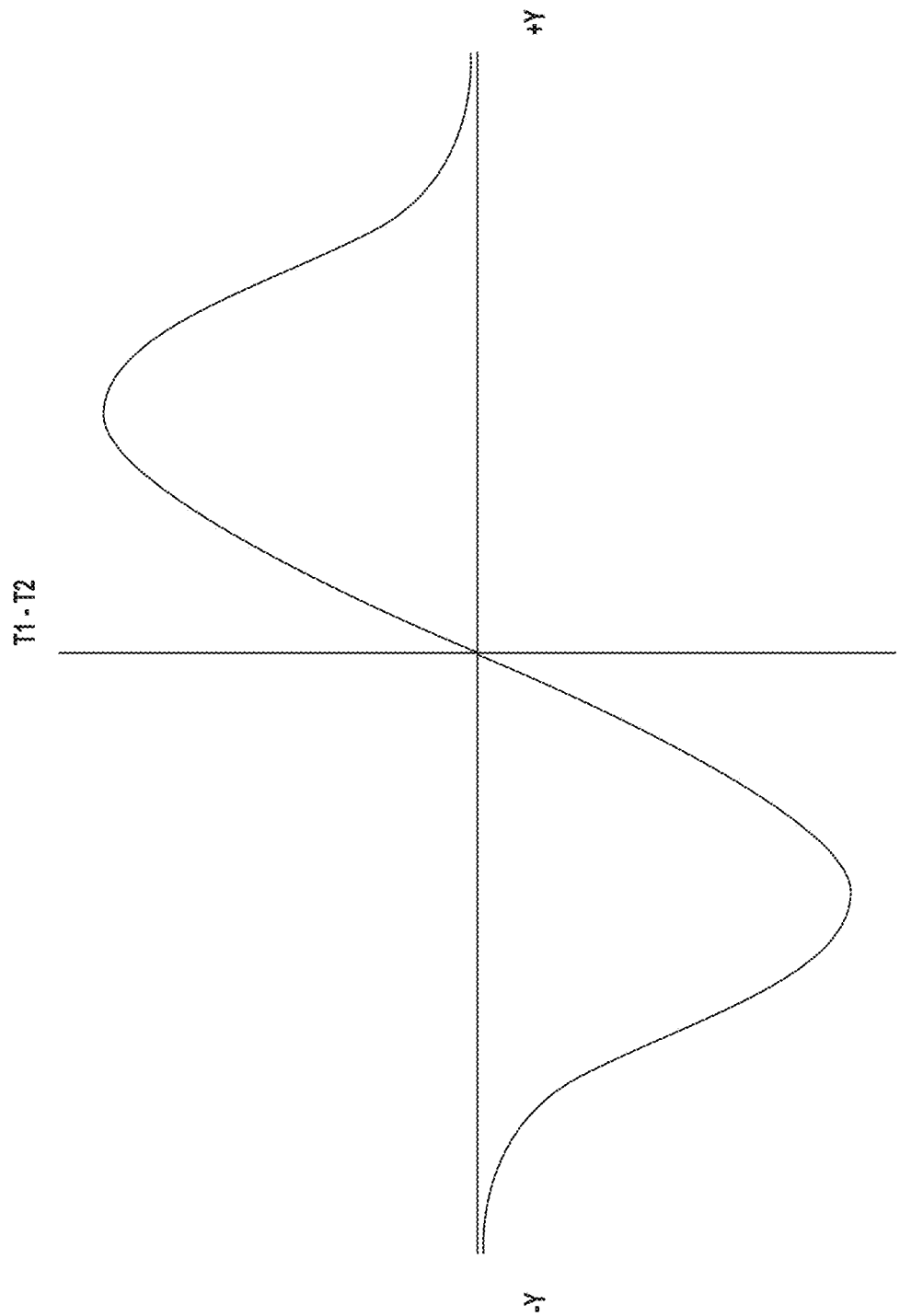

IMPLANT LOCATION DETECTION AND ADAPTIVE TEMPERATURE CONTROL

This application is a continuation of U.S. patent application Ser. No. 17/652,248, which was filed on Feb. 23, 2022, and is entitled, "IMPLANT LOCATION DETECTION AND ADAPTIVE TEMPERATURE CONTROL," which claims the benefit of U.S. Provisional Patent Application No. 63/152,986, filed Feb. 24, 2021, the entire contents of each are incorporated herein by reference.

TECHNICAL FIELD

The disclosure relates to rechargeable implantable medical devices.

BACKGROUND

Medical devices may be external or implanted and may be used to monitor patient signals such as cardiac activity, biological impedance and to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis and other conditions. In some examples, medical devices may include a rechargeable electrical power source, or may be powered directly by transmitting energy through tissue. In some examples, transmitting the energy through the tissue may result in an applied thermal dose, which may be caused by the energy heating the tissue, or heating the implanted device that in turn heats the surrounding tissue.

SUMMARY

In general, the disclosure describes devices, systems, and techniques to determine an energy transfer factor associated with recharging a device and adjust energy delivery based on the energy transfer factor. For example, the system may determine when a power transmitting and receiving system is in an inefficient position, which may cause a thermal response in the device and/or adjacent tissue that less desirable than a more efficient position. In response to detecting the efficiency of the system, the system may also control the levels of energy delivered to the implant based on the detected position. For example, the system may reduce the energy delivered to lower levels when the transmitter and receiver are in an inefficient position relative to a more efficient position to manage the thermal response and the energy transfer.

In one example, this disclosure describes a device comprising a power transmitting unit configured to wirelessly transfer electromagnetic energy to a power receiving unit; and processing circuitry configured to: compute a target output power deliverable by the power transmitting unit for a first duration; control the power transmitting unit to output the target output power based in part on a heat limit; calculate an energy transfer efficiency to the power receiving unit; update an adjustment factor based on the calculated energy transfer efficiency; and apply the adjustment factor to the heat limit for a subsequent duration.

In another example, this disclosure describes a system comprising a power receiving unit; a power transmitting unit configured to wirelessly transfer electromagnetic energy to the power receiving unit; and comprising processing circuitry configured to: compute a target output power deliverable by the power transmitting unit for a first duration; control the power transmitting unit to output the target output power based in part on a heat limit; calculate an energy transfer efficiency to the power receiving unit; update an adjustment factor based on the calculated energy transfer efficiency; and apply the adjustment factor to the heat limit for a subsequent duration.

In another example, this disclosure describes a method comprising computing, by processing circuitry, a target output power deliverable by a wireless power transmitting unit for a first duration; controlling, by the processing circuitry, circuitry to output the target output power based in part on a heat limit; calculating, by the processing circuitry, an energy transfer efficiency to a power receiving unit; and updating, by the processing circuitry, an adjustment factor based on the calculated energy transfer efficiency applying the adjustment factor to the heat limit for a subsequent duration.

The details of one or more examples are set forth in the accompanying drawings and the description below. Other features, objects, and advantages will be apparent from the description, drawings, and claims.

BRIEF DESCRIPTION OF DRAWINGS

FIG. 5F is a graph illustrating an example temperature gradient in the Y direction as described above in FIG. 5E.

DETAILED DESCRIPTION

Figure 1:
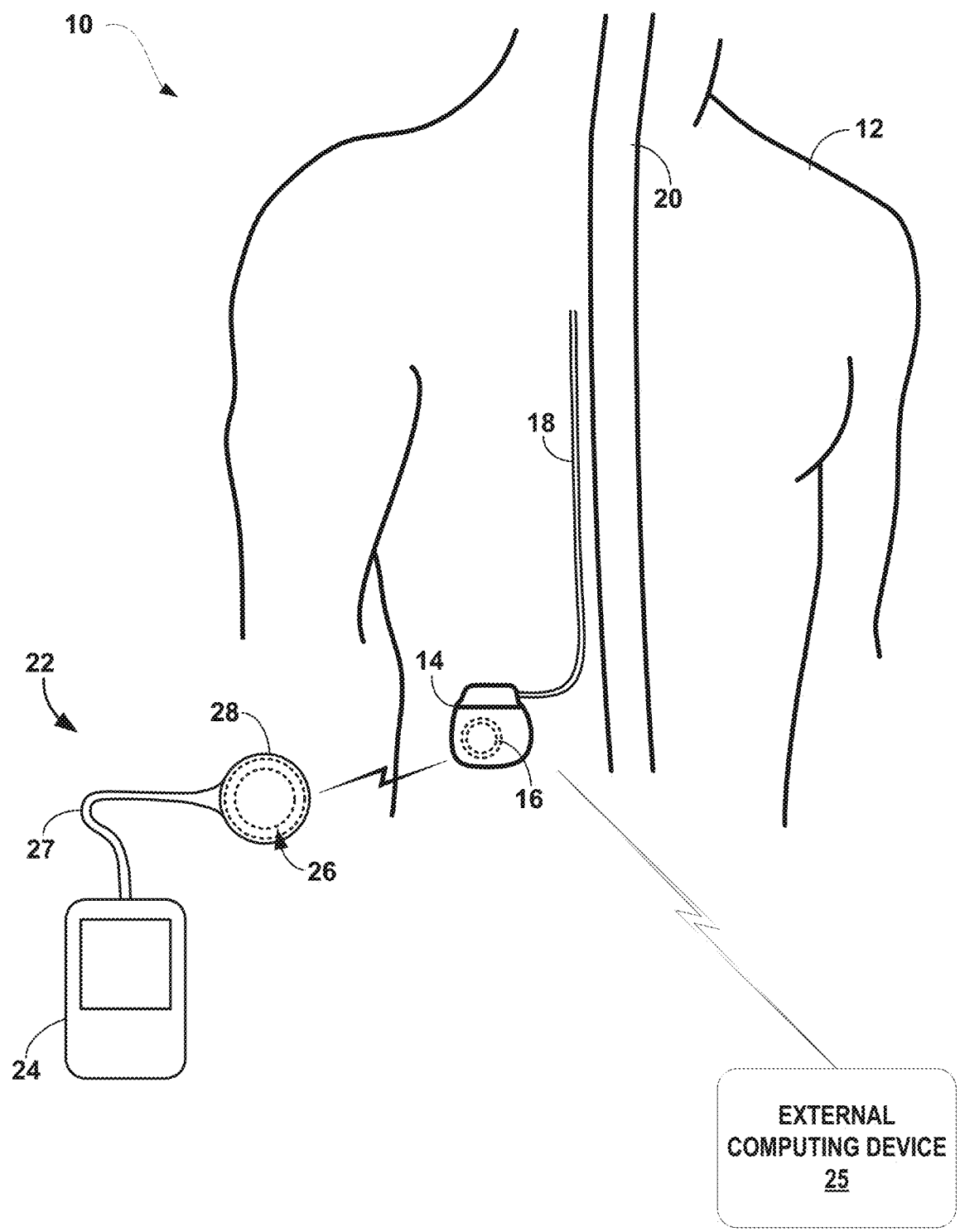
FIG. 1 is a conceptual diagram illustrating example system 10 that includes an implantable medical device (IMD) 14 and an external charging device 22 that charges a rechargeable power source of the IMD 14 via an energy transfer coil 26.

Devices, systems, and techniques are described for determining when a power transmitting and receiving system is in an inefficient position, which may cause a thermal response in a device or adjacent tissue of a patient that is less desirable than a more efficient position. In long term or chronic uses, implantable medical devices may include a rechargeable power source (e.g., one or more capacitors or batteries) that extends the operational life of the medical device to weeks, months, or even years over a non-rechargeable device. When the energy stored in the rechargeable power source has been depleted, the patient may use an external charging device to recharge the power source. In the example of an implantable medical device, the rechargeable power source is implanted in the patient in the power receiving unit (PRU) and the charging device is external of the patient, this charging process may be referred to as transcutaneous charging. In some examples, transcutaneous charging may be performed via inductive coupling between a primary coil in the charging device and a secondary coil in the implantable medical device.

An electrical current applied to the primary coil generates a magnetic field, and when the primary coil is aligned to the secondary coil, the magnetic field induces an electrical current in the secondary coil within the patient. A charging circuit within the implantable medical device then applies current from the secondary coil to charge the rechargeable power source within the implantable medical device. With transcutaneous transfer via inductive coils, the external charging device does not need to physically connect with the rechargeable power source for charging to occur. However, the power transfer efficiency between the two or more devices may change based on the physical orientation of the secondary coil to the primary coil. Inefficient power transfer can lead to transferred power causing eddy currents in metal components that result in heat and/or direct heating of tissue instead of electrical current that charges the rechargeable power source in the implantable medical device. Increased heat can cause patient discomfort, tissue damage, and/or system operational issues.

An example system described herein may adjust power settings and/or provide feedback to a user to readjust one or more components of the system into to a more efficient position. The system described herein may include a power transmitting unit and a power receiving unit. In some examples, the power receiving unit (PRU) is in or coupled to an implantable medical device (IMD). The PRU heat limit and time spent receiving transmitting power may have a direct impact on the thermal response as measured by an applied thermal dose (CEM43) on the PRU, e.g., the implant during a charging session. In the example of a rechargeable PRU, when the system efficiency increases, then the time to recharge may decrease, thereby reducing the applied thermal dose. However, when operating at low efficiency the applied thermal dose may increase, in some examples, because of the increased duration of the recharge time. In some examples, an exacerbating factor is that some poor coupling positions cause a rise to higher temperatures for the same amount of energy input, which may have an exponential effect on the thermal dose. For example, instead of the charging energy being transferred to the battery of the IMD from a target coupling position, the energy may cause increased eddy currents in one or more components of the IMD or cause direct heating of tissue. The thermal dose may be measured based on CEM43, which is a normalizing method to convert the various time-temperature exposures applied into an equivalent exposure time expressed as minutes at the reference temperature of 43° C.

In response to detecting the efficiency of the system, the system may also control the levels of energy delivered to the implant based on the detected relative position. For example, the system may control the energy delivered to lower levels when the transmitter is in an inefficient relative position to the receiver. To optimize the energy transfer, which may reduce recharge time and applied thermal dose, the techniques of this disclosure may include an adaptive recharging algorithm that applies a monotonic transfer function. The transfer function may increase with transfer efficiency to dynamically adjust the heat limit during the charging session. In some examples, for coupling positions in which transfer efficiency is poor, the system may apply the algorithm to reduce the applied heat limit to its lowest allowable value to minimize the applied thermal dose such that the applied thermal dose does not exceed safety limits during the duration of the charging session. The "coupling position" may refer to the relative location, orientation, and angle between the power transmitting unit and the PRU. In other examples, for coupling positions where the IMD efficiency is high, the system may increase the applied heat limit to a maximum allowable value such that the applied thermal dose does not exceed safety limits. In other examples, for coupling positions in the range between poor and high coupling efficiency, the system may adjust the applied heat limit to between the minimum and maximum allowable heat limit. In some examples, the coupling efficiency may be based on efficiency as measured by the PRU and communicated, e.g., wirelessly, to the power transmitting unit, or some other communication receiving device. The heat limit may also be referred to as a "heat control limit" in this disclosure.

FIG. 1 is a conceptual diagram illustrating example system 10 that includes an implantable medical device (IMD) 14 and an external charging device 22 that charges a rechargeable power source of the IMD 14 via an energy transfer coil 26. Although the techniques described in this disclosure are generally applicable to a variety of medical devices including medical devices such as patient monitors, electrical stimulators, or drug delivery devices, application of such techniques to implantable neurostimulators will be described for purposes of illustration. More particularly, the disclosure will refer to an implantable neurostimulation system for use in spinal cord stimulation therapy, but without limitation as to other types of medical devices. An implantable neural stimulator (INS) is an example of an IMD such that one type of IMD is an INS.

As shown in FIG. 1, system 10 includes an IMD 14 and external charging device 22 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally, IMD 14 may be a chronic electrical stimulator that remains implanted within patient 12 for weeks, months, or even years. In the example of FIG. 1, IMD 14 and lead 18 may be directed to delivering spinal cord stimulation therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 includes a rechargeable power source (not shown) and IMD 14 is coupled to lead 18.

Electrical stimulation energy, which may be constant current or constant voltage-based pulses, for example, is delivered from IMD 14 to one or more targeted locations within patient 12 via one or more electrodes (not shown) of lead 18. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Electrical stimulation may be delivered in the form of stimulation pulses or continuous waveforms, for example. In other examples, IMD 14 may be configured to monitor patient biological signals, such as biological impedance, cardiac signals, temperature, activity, and so on. In some examples IMD 14 may not deliver stimulation therapy.

In the example of FIG. 1, lead 18 is disposed within patient 12, e.g., implanted within patient 12. Lead 18 tunnels through tissue of patient 12 from along spinal cord 20 to a subcutaneous tissue pocket or other internal location where IMD 14 is disposed. Although lead 18 may be a single lead, lead 18 may include a lead extension or other segments that may aid in implantation or positioning of lead 18. In addition, a proximal end of lead 18 may include a connector (not shown) that electrically couples to a header of IMD 14. Although only one lead 18 is shown in FIG. 1, system 10 may include two or more leads, each coupled to IMD 14 and directed to similar or different target tissue sites. For example, multiple leads may be disposed along spinal cord 20 or leads may be directed to spinal cord 20 and/or other locations within patient 12. Lead 18 may carry one or more electrodes that are placed adjacent to the target tissue, e.g., spinal cord 20 for spinal cord stimulation (SCS) therapy.

In alternative examples, lead 18 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 18 and IMD 14 may also be configured to provide other types of electrical stimulation or drug therapy (e.g., with lead 18 configured as a catheter). For example, lead 18 may be configured to provide deep brain stimulation (DBS), peripheral nerve stimulation (PNS), or other deep tissue or superficial types of electrical stimulation. In other examples, lead 18 may provide one or more sensors configured to allow IMD 14 to monitor one or more parameters of patient 12. The one or more sensors may be provided in addition to, or in place of, therapy delivery by lead 18.

IMD 14 delivers electrical stimulation therapy to patient 12 via selected combinations of electrodes carried by lead 18. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 18 is tissue proximate spinal cord 20 (e.g., one or more target locations of the dorsal columns or one or more dorsal roots that branch form spinal cord 20. Lead 18 may be introduced into spinal cord 20 via any suitable region, such as the thoracic, cervical, or lumbar regions. Stimulation of dorsal columns, dorsal roots, and/or peripheral nerves may, for example, prevent pain signals from traveling through spinal cord 20 and to the brain of the patient. Patient 12 may perceive the interruption of pain signals as a reduction in pain and, therefore, efficacious therapy results. For treatment of other disorders, lead 18 may be introduced at any exterior location of patient 12.

Although lead 18 is described as generally delivering or transmitting electrical stimulation signals, lead 18 may additionally or alternatively transmit electrical signals from patient 12 to IMD 14 for monitoring. For example, IMD 14 may utilize detected nerve impulses to diagnose the condition of patient 12 or adjust the delivered stimulation therapy. Lead 18 may thus transmit electrical signals to and from patient 12.

A user, such as a clinician or patient 12, may interact with a user interface of an external computing device 25 to communicate with and in some examples, to program IMD 14. Programming of IMD 14 may refer generally to the generation and transfer of commands, programs, or other information to control the operation of IMD 14. For example, the external programmer may transmit programs, parameter adjustments, program selections, group selections, or other information to control the operation of IMD 14, e.g., by wireless telemetry or wired connection.

In some cases, external computing device 25 may be characterized as a physician or clinician programmer if it is primarily intended for use by a physician or clinician. In other cases, external computing device 25 may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by the stimulator, e.g., IMD 14, whereas a patient programmer may support adjustment and selection of such programs by a patient during ordinary use. In other examples, external charging device 25 may be included, or part of, an external programmer. In this manner, a user may program and charge IMD 14 using one device, or multiple devices.

IMD 14 may be constructed of any polymer, metal, or composite material sufficient to house the components of IMD 14 within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The housing of IMD 14 may be configured to provide a hermetic seal for components, such as a rechargeable power source. In addition, the housing of IMD 14 may be selected of a material that facilitates receiving energy to charge a rechargeable power source.

As described herein, secondary coil 16 may be included within IMD 14. However, in other examples, secondary coil 16 could be located external to a housing of IMD 14, separately protected from fluids of patient 12, and electrically coupled to electrical components of IMD 14. This type of configuration of IMD 14 and secondary coil 16 may provide implant location flexibility when anatomical space available for implantable devices is minimal and/or improved inductive coupling between secondary coil 16 and primary coil 26. In any case, an electrical current may be induced within secondary coil 16 to charge the battery of IMD 14 when energy transfer coil 26 (e.g., a primary coil) produces a magnetic field that is aligned with secondary coil 16. The induced electrical current may first be conditioned and converted by a charging module (e.g., a charging circuit) to an electrical signal that can be applied to the battery with an appropriate charging current. For example, the inductive current may be an alternating current that is rectified to produce a direct current suitable for charging the battery. In some examples, primary coil 26 may comprise multiple separate coils that are displaced in location from each other.

The rechargeable power source of IMD 14 may include one or more capacitors, batteries, or other components (e.g., chemical, or electrical energy storage devices). Example batteries may include lithium-based batteries, nickel metal-hydride batteries, or other materials. The rechargeable power source may be replenished, refilled, or otherwise capable of increasing the amount of energy stored after energy has been depleted. The energy received from secondary coil 16 may be conditioned and/or transformed by a charging circuit. The charging circuit may then send an electrical signal used to charge the rechargeable power source when the power source is fully depleted or only partially depleted.

Charging device 22 may be used to recharge the rechargeable power source within IMD 14 implanted in patient 12. Charging device 22 may be a hand-held device, a portable device, or a stationary charging system. In any case, charging device 22 may include components necessary to charge IMD 14 through tissue of patient 12. Charging device 22 may include housing 24 and energy transfer coil 26, also referred to as primary coil 26. In addition, heat sink device 28 may be removably attached to energy transfer coil 26 to manage the temperature of then energy transfer coil during charging sessions. Housing 24 may enclose operational components such as a processor, memory, user interface, telemetry module, power source, and charging circuit configured to transmit energy to secondary coil 16 via energy transfer coil 26. Although a user may control the recharging process with a user interface of charging device 22, charging device 22 may alternatively be controlled by another device (e.g., an external programmer such as external computing device 25). In other examples, charging device 22 may be integrated with an external programmer, such as a patient programmer carried by patient 12.

Charging device 22 and IMD 14 may utilize any wireless power transfer techniques that are capable of recharging the power source of IMD 14 when IMD 14 is implanted within patient 14. In one example, system 10 may utilize inductive coupling between primary coils (e.g., energy transfer coil 26) and secondary coils (e.g., secondary coil 16) of charging device 22 and IMD 14. In inductive coupling, energy transfer coil 26 is placed near implanted IMD 14 such that energy transfer coil 26 is aligned with secondary coil 16 of IMD 14. Charging device 22 may then generate an electrical current in energy transfer coil 26 based on a selected power level for charging the rechargeable power source of IMD 14. When the primary and secondary coils are aligned, the electrical current in the primary coil may magnetically induce an electrical current in the secondary coil within IMD 14. Since the secondary coil is associated with and electrically coupled to the rechargeable power source, the induced electrical current may be used to increase the voltage, or charge level, of the rechargeable power source. Although inductive coupling is generally described herein, any type of wireless energy transfer may be used to transfer energy between charging device 22 and IMD 14.

Energy transfer coil 26 may include a wound wire (e.g., a coil) (not shown in FIG. 1). The coil may be constructed of a wire wound in an in-plane spiral (e.g., a disk-shaped coil). In some examples, this single or even multi-layers spiral of wire may be considered a flexible coil capable of deforming to conform with a non-planar skin surface. The coil may include wires that electrically couple the flexible coil to a power source and a charging module configured to generate an electrical current within the coil. Energy transfer coil 26 may also include a housing that encases the coil. The housing may be constructed of a flexible material such that the housing promotes, or does not inhibit, flexibility of the coil. Energy transfer coil 26 may be external of housing 24 such that energy transfer coil 26 can be placed on the skin of patient 12 proximal to IMD 14. In this manner, energy transfer coil 26 may be tethered to housing 24 using cable 27 or other connector that may be between approximately a few inches and several feet in length. In other examples, energy transfer coil 26 may be disposed on the outside of housing 24 or even within housing 24. Energy transfer coil 26 may thus not be tethered to housing 22 in other examples.

Heat sink device 28 may be removably attached to energy transfer coil 26. In examples where energy transfer coil 26 is disposed on or within housing 24, heat sink device 28 may be configured to be removably attached to housing 24.

Together, system 10 may include energy transfer coil 26 and heat sink device 28. Energy transfer coil 26 may be configured to recharge a rechargeable power source of IMD 14. In the example of system 10, charging device 22 is the power transmitting unit and IMD 14 is the power receiving unit. IMD 14 may be in a flipped or non-flipped position.

Heat sink device 28 may include a housing that contains a phase change material. The housing may be configured to be removably attached to energy transfer coil 26. In this manner, the system may operate such that energy transfer coil 26 generates heat during a recharge session and the phase change material of heat sink device 28 absorbs at least a portion of the generated heat. When the phase change material is at the melting temperature, the heat may contribute to the heat of fusion of the phase change material and not to increasing the temperature of energy transfer coil 26.

A flexible coil of energy transfer coil 26 may be formed by one or more coils of wire. In one example the coil is formed by a wire wound into a spiral within a single plane (e.g., an in-plane spiral). This in-plane spiral may be constructed with a thickness equal to the thickness of the wire, and the in-plane spiral may be capable of transferring energy with another coil. In other examples, the coil may be formed by winding a coil into a spiral bent into a circle. However, this type of coil may not be as thin as the in-plane spiral.

A variety of system metrics are available to external charging device 22 from its own computations of power and heat and from metrics communicated to the recharger from IMD 14. In this disclosure charging device 22 may also be referred to as recharger 22. These metrics may include but are not limited to battery current (Iimd_batt)—for fixed power levels or speeds, power transfer efficiency (Pimd_batt/Ptank), IMD Efficiency (Pimd_batt/$Q_{IMD}$) or (Pimd_batt/Pimd). Analysis of system characterization data that the IMD efficiency, which may be measured by IMD 14 and communicated to external charging device 22, may be a good indicator of when the recharger primary coil 26 is concentric with secondary coil 16. A concentric relative position of primary coil 26 and secondary coil 16 may be in positions with the lowest overall transient thermal response (increase in temp for the same heat). In some examples, the energy transfer in concentric positions (e.g., near 0, −20 in X and Y) may be higher and the battery of IMD 14 may charge faster. Therefore, there may be an exponential relationship between the IMD efficiency, which may also be referred to as INS efficiency in this disclosure, and the overall thermal dose in units of CEM43.

The power transfer efficiency on the other hand may be more skewed towards the geometrical center of the IMD (near 0, 0 in X and Y). In some examples both power transfer efficiency and IMD efficiency metrics may be lower when primary coil 26 is positioned over the header of IMD 14, which may lead to decreased efficiency and a less desirable thermal profile (e.g., an increase in temperature for the same heat) caused by the thermal response in the device and/or adjacent tissue. Furthermore, at such positions the time to charge may be longer so the overall thermal dose may be worse than for shorter and quicker charging periods that result from a more efficient coupling.

The system of this disclosure may use a variety of techniques to adapt an algorithm and heat doses to reduce the thermal dose for less desirable, e.g., less efficient, relative positions between primary coil 26 and secondary coil 16. System 10 may include techniques to increase the charging speed or charging rate for more desirable relative positions of energy transfer coil 26 and secondary coil 16, and thereby reduce charging time and thermal dose.

Processing circuitry of charging device 22, or other processing circuitry in system 10, may calculate the heat at IMD 14. Charging device 22 may calculate $P_{TANK}$, which is the power sent to primary coil 26 and may include the inductance and capacitance between power generation circuitry and primary coil 26. Charging device 22 may measure the heat lost by primary coil 26 ($Q_{PRIM}$), for example by receiving signals from a temperature sensor within primary coil 26. The heat lost by primary coil 26 ($Q_{PRIM}$) may also be described as the amount of energy sent to primary coil 26 is not wirelessly transmitted to IMD 14 but is instead lost to heating primary coil 26 and associated structure around charging coil 26. Charging device 22 may receive wireless communication from IMD 14 that includes an indication of the amount of power delivered to the electrical energy storage device of IMD 14 (Pimd_batt). Therefore, charging device 22 may calculate the heat at IMD 14 based on:

$$Q_{IMD}=P_{TANK}-Q_{PRIM}-\text{Pimd\_batt}$$

Therefore $Q_{IMD}$, as defined above may include heat generated by IMD 14, as well as generated in tissue surrounding IMD 14. $Q_{IMD}$ may provide a conservative estimate, e.g., leave a safety margin, because $Q_{IMD}$ assumes any energy output by the primary coil and not converted to power delivered to the device (Pimd_batt), or lost to heat at the primary coil ($Q_{PRIM}$) becomes heat at IMD 14.

In some examples, processing circuitry of system 10 may multiply the heat limits for IMD 14 in different power transfer modes (or in the highest speed mode) by an adjustment factor (AF). The AF may be configured as a function of the IMD efficiency and the range of possible values on AF may be set as from 0 to 1. For example, for the dynamically set heat limit for IMD 14:

Heat Limit=AF*maximum Heat limit, where
 IMD efficiency=Pimd_batt/$Q_{IMD}$, and
 Total efficiency=Pimd_batt/Ptank In this disclosure, AF may be a function of IMD efficiency. In some examples, AF may be linear or non-linear. A linear example may include AF=m*IMD efficiency+b. In other examples, AF may be bounded so that a predetermined zone of measured IMD efficiency, as transmitted to charging system 22, is set to a specific value, such as:

minimum(m*IMD Efficiency+b, maximum IMD heat limit)
OR
maximum[minimum(m*IMD Efficiency+b, maximum IMD heat limit), minimum (IMD heat limit)].

In other examples, instead of a piecewise linear function, the adjustment factor may be set by another form of a piecewise function, such as an S-curve using a sigmoid function, logistic function, or similar function. For example, with a logistic function:

$$AF=\text{maximum IMD heat}/(1+e^{\char`\^}(k*(\text{IMD Efficiency}-\text{IMD Efficiency Center Point})))$$

In this way, the adjustment factor may include a smooth transition of recharge heat levels allowed from the good positions to the less desirable positions. Additional options for adjustment factor may include more binary and conditional logic, for example:

if IMD Efficiency<X,
 then use heat control limit A,
 otherwise use heat control limit B.

In other examples, if efficiency persists to be less than a certain value, e.g., for longer than a predetermined duration, then exit the high-power phase and transmit energy at lower power settings. In other examples, system 10 may implement the adjustment factor as a look up table between IMD efficiency and AF. In some examples, it may be desirable to have the adjustment factor adjusted at a slower rate, e.g., less often, than the algorithm controlling the $Q_{IMD}$ limit to avoid oscillations in the control algorithm.

In other words, system 10 may measure efficiency, such as IMD efficiency, to determine whether the relative position of primary coil 26 and secondary coil 16 may be in a less desirable relative position. Processing circuitry of system 10, e.g., processing circuitry of charging system 22, processing circuitry of external computing device 25, and/or processing circuitry of IMD 14, may calculate a new limit, such as using one of the techniques described above based on the measured efficiency. System 10 may then adjust power transmitted based on the newly calculated limit.

In other examples, system 10 may also detect hot spots based on multiple thermistors. In some examples, IMD 14 may include temperature sensors at a plurality of locations within the implant, for example within the header or near the header. One of the temperature sensors may be located near the center of the device or on the can in the center of the recharge coil. When another sensor is significantly hotter than the central sensor, e.g., a temperature differential that satisfies a temperature threshold, the algorithm may scale the energy transfer and charge slower or faster as needed. In some examples, the primary coil may also include one or more temperature sensors.

In some examples, different portions of IMD 14 may increase in temperature more than other portions. The differences may be caused by the type of material, the arrangement of components in relation to secondary coil 16, or for other reasons. In some examples, the temperature of portions of IMD 14 may change based on the relative position of primary coil 26 to the IMD 14. In some examples, the header of IMD 14 may be sensitive to the relative position of primary coil 26, which in some examples may be caused by eddy currents.

In other examples, IMD 14 may include multiple secondary coils. Each of the coils may be located in a different position on IMD 14, for example in a first side and on a second side opposite the first side. In some examples, IMD 14 may determine that a first coil is receiving more electromagnetic energy than other coils of the multiple secondary coils and therefore determine an approximate relative location of the primary coil.

Processing circuitry of system 10 may determine if primary coil 26 is over the header of IMD 14 by using system metrics for, e.g., IMD charging efficiency (Pimd_batt/$Q_{IMD}$). In some examples, processing circuitry of system 10 may decide how to behave differently when in one of these relative positions. The processing circuitry may execute other techniques to determine charge rate, such as a proportional-integral-derivative controller (PID controller or three-term controller) as a control loop mechanism. In some examples processing circuitry may employ a digital low-pass filter (LPF), such as a 2-pole, or similar LPF.

The recharger, e.g., charging device 22, may compute IMD_efficiency during closed loop recharge according to the equation: IMD_efficiency=Pimd_batt/$Q_{IMD}$. If the Pimd_batt is zero, the efficiency may be returned as zero. The processing circuitry of the recharger may adjust the current $Q_{IMD}$ limit by an adjustment factor according to a look up table, or some other technique for determining the adjustment factor described above. The adjustment factor may be bounded between 0 and 1 and be updated periodically. An adaptive algorithm, also called an adaptive recharge algorithm, executed by processing circuitry of system 10 may use a variety of system metrics. Examples of system metric options may include various energy transfer efficiency measurements, including:

IMB Battery Current (mA) in a given phase or power level

Total Efficiency Pimd_batt/Ptank (%)

IMD Efficiency Pimd_batt/$Q_{IMD}$ (%)–Recommendation

IMD Current inefficiency $Q_{IMD}$/Iimd_batt (V) or efficiency Iimd_batt/$Q_{IMD}$ (1/V)

Figure 2:
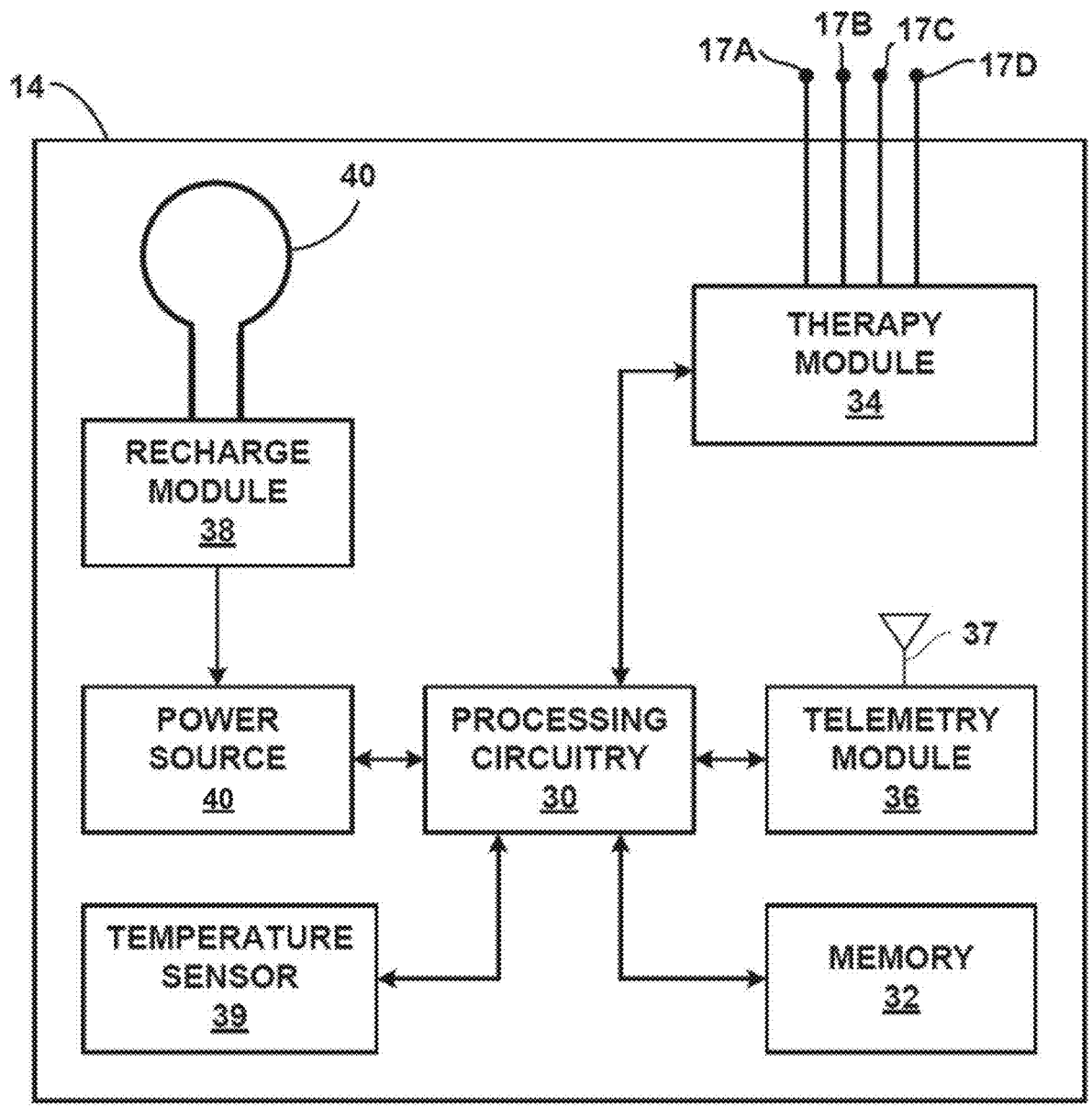
FIG. 2 is a block diagram illustrating example components of IMD 14 of FIG. 1.

FIG. 2 is a block diagram illustrating example components of IMD 14 of FIG. 1. In the example illustrated in FIG. 2, IMD 14 includes temperature sensor 39, coil 40, processing circuitry 30, therapy module 34, recharge module 38, memory 32, telemetry module 36, and rechargeable power source 40. In other examples, IMD 14 may include a greater or a fewer number of components. In general, IMD 14 may comprise any suitable arrangement of hardware, alone or in combination with software and/or firmware, to perform the various techniques described herein attributed to IMD 14 and processing circuitry 30, and any equivalents thereof.

Processing circuitry 30 of IMD 14 may include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 may include a memory 32, such as random-access memory (RAM), read only memory (ROM), programmable read only memory (PROM), erasable programmable read only memory (EPROM), electronically erasable programmable read only memory (EEPROM), flash memory, comprising executable instructions for causing the processing circuitry 30 to perform the actions attributed to this circuitry. Moreover, although processing circuitry 30, therapy module 34, recharge module 38, telemetry module 36, and temperature sensor 39 are described as separate modules, in some examples, some combination of processing circuitry 30, therapy module 34, recharge module 38, telemetry module 36 and temperature sensor 39 are functionally integrated. In some examples, processing circuitry 30, therapy module 34, recharge module 38, telemetry module 36, and temperature sensor 39 correspond to individual hardware units, such as ASICs, DSPs, FPGAs, or other hardware units. As described above in relation to FIG. 1, temperature sensor 39 may comprise one or more temperature sensors in different locations on IMD 14.

Memory 32 may store therapy programs or other instructions that specify therapy parameter values for the therapy provided by therapy module 34 and IMD 14. In some examples, memory 32 may also store temperature data from temperature sensor 39, instructions for recharging rechargeable power source 40, thresholds, instructions for communication between IMD 14 and external charging device 22, or any other instructions required to perform tasks attributed to IMD 14. Memory 32 may be configured to store instructions for communication with and/or controlling one or more temperature sensors of temperature sensor 39. In various examples, memory 32 stores information related to determining the temperature of housing 19 and/or exterior surface(s) of housing 19 of IMD 14 based on temperatures sensed by one or more temperature sensors, such as temperature sensor 39, located within IMD 14.

For example, memory 32 may store one or more formulas, as further described below, that may be used to determine the temperature of the housing 19 and/or exterior surface(s) of housing 19 based on temperature(s) sensed by the temperature sensor 39. Memory 32 may store values for one or more determined constants used by these formulas. Memory 32 may store instructions that, when executed by processing circuitry such as processing circuitry 30, perform an algorithm, including using the formulas, to determine a current temperature, or temperatures over time, for the housing 19 and/or exterior surface(s) of the housing 19 of IMD 14 during a charging session and/or for some time after a charging session performed on IMD 14. In some examples, memory 32 may store instructions that, when executed by processing circuitry such as processing circuitry 30, perform an algorithm, including using one or more formulas, to determine a value to be assigned to one or more of the constants used in the algorithm to determine a temperature for the housing 19 and/or exterior surface(s) of the housing 19 of IMD 14 during a charging session and/or for some time after a charging session performed on IMD 14.

Generally, therapy module 34 may generate and deliver electrical stimulation under the control of processing circuitry 30. In some examples, processing circuitry 30 controls therapy module 34 by accessing memory 32 to selectively access and load at least one of the stimulation programs to therapy module 34. For example, in operation, processing circuitry 30 may access memory 32 to load one of the stimulation programs to therapy module 34. In such examples, relevant stimulation parameters may include a voltage amplitude, a current amplitude, a pulse rate, a pulse width, a duty cycle, or the combination of electrodes 17A, 17B, 17C, and 17D (collectively "electrodes 17") that therapy module 34 uses to deliver the electrical stimulation signal. Therapy module 34 may be configured to generate and deliver electrical stimulation therapy via one or more of electrodes 17A, 17B, 17C, and 17D of lead 18. Alternatively, or additionally, therapy module 34 may be configured to provide different therapy to patient 12. For example, therapy module 34 may be configured to deliver drug delivery therapy via a catheter. These and other therapies may be provided by IMD 14.

IMD 14 also includes components to receive power from external charging device 22 to recharge rechargeable power source 40 when rechargeable power source 40 has been at least partially depleted. As shown in FIG. 2, IMD 14 includes secondary coil 40 and recharge module 38 coupled to rechargeable power source 40. Recharge module 38 may be configured to charge rechargeable power source 40 with the selected power level determined by either processing circuitry 30 or external charging device 22. Recharge module 38 may include any of a variety of charging and/or control circuitry configured to process or convert current induced in coil 40 into charging current to charge power source 40. Although processing circuitry 30 may provide some commands to recharge module 38, in some examples, processing circuitry 30 may not need to control any aspect of recharging.

Secondary coil 40 may include a coil of wire or other device capable of inductive coupling with a primary coil disposed external to patient 12. Although secondary coil 40 is illustrated as a simple loop of in FIG. 2, secondary coil 40 may include multiple turns of conductive wire. Secondary coil 40 may include a winding of wire configured such that an electrical current can be induced within secondary coil 40 from a magnetic field. The induced electrical current may then be used to recharge rechargeable power source 40. In this manner, the electrical current may be induced in secondary coil 40 associated with rechargeable power source 40. The induction may be caused by electrical current generated in the primary coil of external charging device 22, where the level of the current may be based on the selected power level. The coupling between secondary coil 40 and the primary coil of external charging device 22 may be dependent upon the alignment of the two coils. Generally, the coupling efficiency may increase when the two coils share a common axis and are in close proximity to each other. External charging device 22 and/or IMD 14 may provide one or more audible tones or visual indications of the alignment.

Although inductive coupling is generally described as the method for recharging rechargeable power source 40, other wireless energy transfer techniques may alternatively be used (such as RF energy transfer). Any of these techniques may generate heat in IMD 14 such that the charging process may need to be controlled by matching the determined temperature to one or more thresholds, modeling tissue temperatures based on the determined temperature, or using a calculated cumulative thermal dose as feedback.

Recharge module 38 may include one or more circuits that process, filter, convert and/or transform the electrical signal induced in the secondary coil to an electrical signal capable of recharging rechargeable power source 40. For example, in alternating current induction, recharge module 38 may include a half-wave rectifier circuit and/or a full-wave rectifier circuit configured to convert alternating current from the induction to a direct current for rechargeable power source 40. The full-wave rectifier circuit may be more efficient at converting the induced energy for rechargeable power source 40. However, a half-wave rectifier circuit may be used to store energy in rechargeable power source 40 at a slower rate. In some examples, recharge module 38 may include both a full-wave rectifier circuit and a half-wave rectifier circuit such that recharge module 38 may switch between each circuit to control the charging rate of rechargeable power source 40 and temperature of IMD 14.

Rechargeable power source 40 may include one or more capacitors, batteries, and/or other energy storage devices. Rechargeable power source 40 may deliver operating power to the components of IMD 14. In some examples, rechargeable power source 40 may include a power generation circuit to produce the operating power. Rechargeable power source 40 may be configured to operate through many discharge and recharge cycles. Rechargeable power source 40 may also be configured to provide operational power to IMD 14 during the recharge process. In some examples, rechargeable power source 40 may be constructed with materials to reduce the amount of heat generated during charging. In other examples, IMD 14 may be constructed of materials and/or using structures that may help dissipate generated heat at rechargeable power source 40, recharge module 38, and/or secondary coil 40 over a larger surface area of the housing of IMD 14.

Although rechargeable power source 40, recharge module 38, and secondary coil 40 are shown as contained within the housing of IMD 14, in alternative implementations, at least one of these components may be disposed outside of the housing. For example, in some implementations, secondary coil 40 may be disposed outside of the housing of IMD 14 to facilitate better coupling between secondary coil 40 and the primary coil of external charging device 22. These different configurations of IMD 14 components may allow IMD 14 to be implanted in different anatomical spaces or facilitate better inductive coupling alignment between the primary and secondary coils.

IMD 14 may also include temperature sensor 39. Temperature sensor 39 may include one or more temperature sensors configured to measure the temperature of respective portions of IMD 14. As described herein, these temperature sensor(s) may not be thermally coupled to, and may not be directly attached to, the portion of the device for which a temperature is to be determined based on the sensed temperature measured by temperature sensor 39. In one instance, the temperature sensor is not directly attached to the housing 19 or to the exterior surface(s) of housing 19 of the device. In other words, temperature measurement is not performed through direct contact or physical contact between the temperature sensor and the target portion to be measured. Although the temperature sensor may be physically attached to the target portion or target surface through one or more structures, thermal conduction that may occur between the target portion and the sensor is not directly used to measure the temperature of the target portion.

Temperature sensor 39 may be arranged to measure the temperature of a component, surface, or structure, e.g., secondary coil 40, power source 40, recharge module 38, and other circuitry housed within IMD 14. Temperature sensor 39 may be disposed internal of the housing of IMD 14 or otherwise disposed relative to the external portion of housing (e.g., tethered to an external surface of housing via an appendage cord, light pipe, heat pipe, or some other structure). As described herein, temperature sensor 39 may be used to make temperature measurements of internal portions of the IMD 14, the temperature measurements used as a basis for determining the temperature of the housing and/or external surface of IMD 14. For example, processing circuitry 30 or processing circuitry of external charging device 22 may use these temperature measurements to determine the housing/external surface temperatures of IMD 14.

In other examples, temperature measurements may be used to determine temperatures of a specific portion of housing 19 or a component coupled thereto, such as header block 15, or another module that is coupled to IMD 14. For instance, IMD 14 may comprise an additional housing that is separate from, but affixed to, housing 19 that contains some components of IMD 14. As one specific example, a secondary coil such as secondary coil 40 may reside within an additional housing that is external to, but affixed to, main housing 19.

Temperature measurements may be used to determine a temperature of a surface or portion of this additional housing or a structure within this housing such as the secondary coil itself. As another example, IMD 14 may carry an appendage protruding from housing 19 carrying one or more electrodes that serves as a stub lead for delivering electrical stimulation therapy. Temperature sensor 39 may be used to make temperature measurements that may be used as a basis for determining the temperature of a portion of this structure. The determined temperatures are then further used as feedback to control the power levels or charge times (e.g., cycle times) used during the charging session of rechargeable power source 40. In some examples, temperature sensor 39 may be used to obtain temperature measurements of a header block 15, or another module that is coupled to IMD 14. For instance, IMD 14 may comprise an additional housing that is separate from, but affixed to, housing 19 that contains some components of IMD 14. As one specific example, a secondary coil may reside within an additional housing. As another example, IMD 14 may carry an appendage protruding from housing 19 carrying one or more electrodes that serves as a stub lead for delivering electrical stimulation therapy. Temperature sensor 39 may be used to make temperature measurements that may be used as a basis for determining the temperature of a surface, or another portion, of these and other structures.

Although a single temperature sensor may be adequate, multiple temperature sensors may provide more specific temperature readings of separate components or of different portions of the IMD. Although processing circuitry 30 may continuously measure temperature using temperature sensor 39, processing circuitry 30 may conserve energy by only measuring temperatures during recharge sessions. Further, temperatures may be sampled at a rate necessary to effectively control the charging session, but the sampling rate may be reduced to conserve power as appropriate. Processing circuitry 30 may be configured to access memory, such as memory 32, to retrieve information comprising instructions, formulas, determined values, and/or one or more constants, and to use this information to execute an algorithm to determine a current temperature, and/or a series of temperatures over time, for the housing 19 and/or exterior surface(s) of housing 19 of IMD 14 based on the measured temperature(s) provided by temperature sensor 39.

Processing circuitry 30 may also control the exchange of information with external charging device 22 and/or an external programmer using telemetry module 36. Telemetry module 36 may be configured for wireless communication using radio frequency protocols, such as BLUETOOTH, or similar RF protocols, as well as using inductive communication protocols. Telemetry module 36 may include one or more antennas 37 configured to communicate with external charging device 22, for example. Processing circuitry 30 may transmit operational information and receive therapy programs or therapy parameter adjustments via telemetry module 36. Also, in some examples, IMD 14 may communicate with other implanted devices, such as stimulators, control devices, or sensors, via telemetry module 36. In addition, telemetry module 36 may be configured to control the exchange of information related to sensed and/or determined temperature data, for example temperatures sensed by and/or determined from temperatures sensed using temperature sensor 39. In some examples, telemetry module 36 may communicate using inductive communication, and in other examples, telemetry module 36 may communicate using RF frequencies separate from the frequencies used for inductive charging.

In some examples, processing circuitry 30 may transmit additional information to external charging device 22 related to the operation of rechargeable power source 40. For example, processing circuitry 30 may use telemetry module 36 to transmit indications that rechargeable power source 40 is completely charged, rechargeable power source 40 is fully discharged, or any other charge status of rechargeable power source 40. In some examples, processing circuitry 30 may use telemetry module 36 to transmit instructions to external charging device 22, including instructions regarding further control of the charging session, for example instructions to lower the power level or to terminate the charging session, based on the determined temperature of the housing/external surface 19 of the IMD.

Processing circuitry 30 may also transmit information to external charging device 22 that indicates any problems or errors with rechargeable power source 40 that may prevent rechargeable power source 40 from providing operational power to the components of IMD 14. In various examples, processing circuitry 30 may receive, through telemetry module 36, instructions for algorithms, including formulas and/or values for constants to be used in the formulas, that may be used to determine the temperature of the housing 19 and/or exterior surface(s) of housing 19 of IMD 14 based on temperatures sensed by temperature sensor 39 located within IMD 14 during and after a recharging session performed on rechargeable power source 40.

Figure 3:
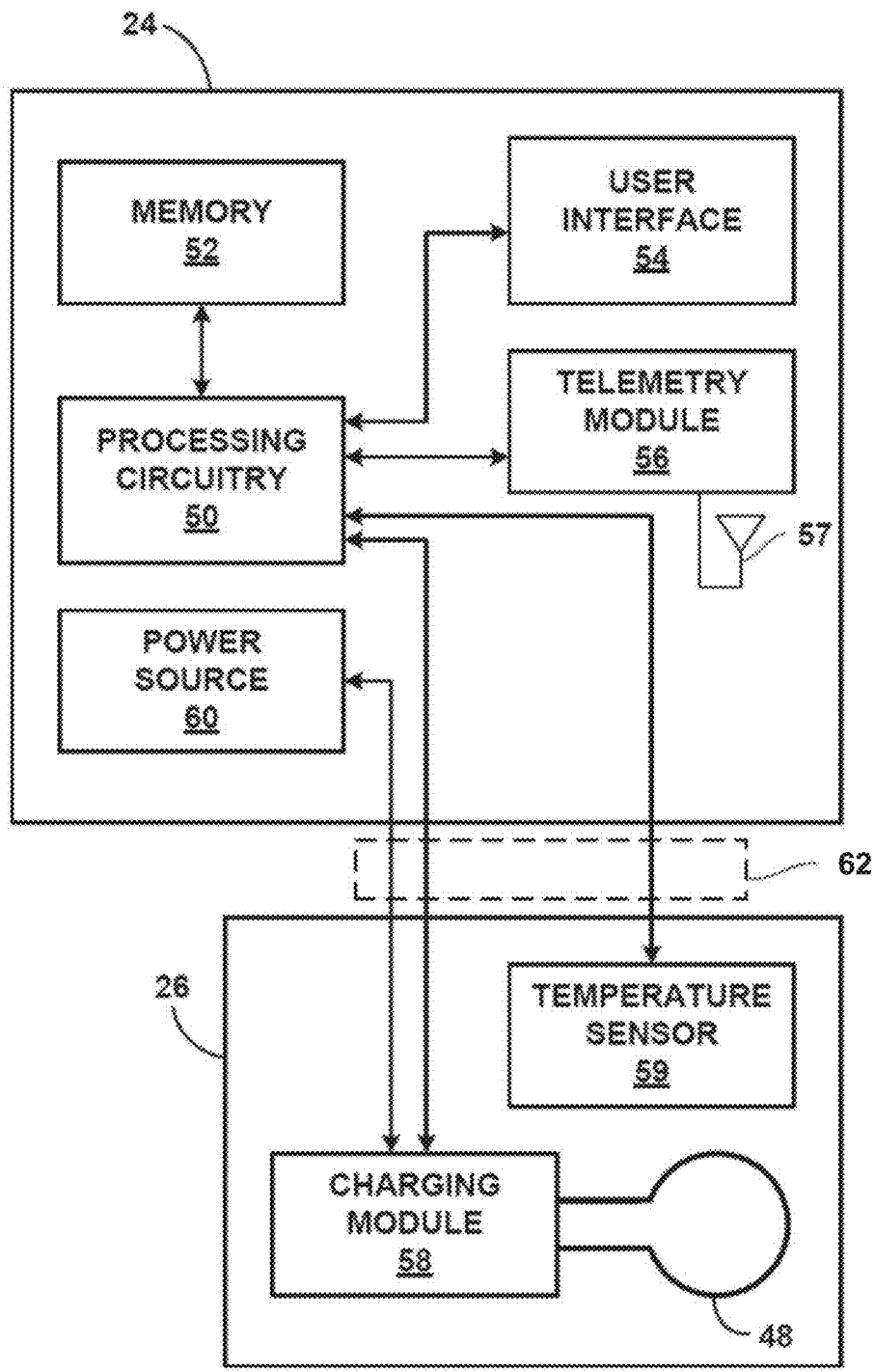
FIG. 3 is a block diagram of an example external charging device 22 of FIG. 1.

FIG. 3 is a block diagram of an example external charging device 22 of FIG. 1 and may also be referred to as recharger 22. While external charging device 22 may generally be described as a hand-held device, external charging device 22 may be a larger portable device or a more stationary device. In addition, in other examples external charging device 22 may be included as part of an external programmer or include functionality of an external programmer. External charging device 22 may also be configured to communicate with an external programmer. As shown in FIG. 3, external charging device 22 includes two separate components. Housing 24 encloses components such as a processing circuitry 50, memory 52, user interface 54, telemetry module 56, and power source 60. Charging head 26 may include charging module 58, temperature sensor 59, and coil 48. As shown in FIG. 2, housing 24 is electrically coupled to charging head 26 via charging cable 62. Charging head 26 is an example of energy coil 26, e.g., primary coil 26, described above in relation to FIG. 1.

A separate charging head 26 may facilitate optimal positioning of coil 48 over coil 40 of IMD 14. However, charging module 58 and/or coil 48 may be integrated within housing 24 in other examples. Memory 52 may store instructions that, when executed by processing circuitry 50, causes processing circuitry 50 and external charging device 22 to provide the functionality ascribed to external charging device 22 throughout this disclosure, and/or any equivalents thereof.

External charging device 22 may also include one or more temperature sensors, illustrated as temperature sensor 59, similar to temperature sensor 39 of FIG. 2. As shown in FIG. 3, temperature sensor 59 may be disposed within charging head 26. In other examples, one or more temperature sensors of temperature sensor 59 may be disposed within housing 24. For example, charging head 26 may include one or more temperature sensors positioned and configured to sense the temperature of coil 48 and/or a surface of the housing of charging head 26. In some examples, external charging device 22 may not include temperature sensor 59.

In general, external charging device 22 comprises any suitable arrangement of hardware, alone or in combination with software and/or firmware, to perform the techniques ascribed to external charging device 22, and processing circuitry 50, user interface 54, telemetry module 56, and charging module 58 of external charging device 22, and/or any equivalents thereof. In various examples, external charging device 22 may include one or more processors, such as one or more microprocessors, DSPs, ASICs, FPGAs, or any other equivalent integrated or discrete logic circuitry, as well as any combinations of such components. External charging device 22 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processing circuitry 50, telemetry module 56, charging module 58, and temperature sensor 59 are described as separate modules, in some examples, processing circuitry 50, telemetry module 56, charging module 58, and/or temperature sensor 59 are functionally integrated. In some examples, processing circuitry 50, telemetry module 56, charging module 58, and/or temperature sensor 59 correspond to individual hardware units, such as ASICs, DSPs, FPGAs, or other hardware units.

Memory 52 may store instructions that, when executed by processing circuitry 50, cause processing circuitry 50 and external charging device 22 to provide the functionality ascribed to external charging device 22 throughout this disclosure, and/or any equivalents thereof. For example, memory 52 may include instructions that cause processing circuitry 50 to control the power level used to charge IMD 14 in response to the determined temperatures for the housing/external surface(s) of IMD 14, as communicated from IMD 14, or instructions for any other functionality. In addition, memory 52 may include a record of selected power levels, sensed temperatures, determined temperatures, or any other data related to charging rechargeable power source 40. Processing circuitry 50 may, when requested, transmit any of this stored data in memory 52 to another computing device for review or further processing. Processing circuitry 50 may be configured to access memory, such as memory 32 of IMD 14 and/or memory 52 of external charging device 22, to retrieve information comprising instructions, formulas, and determined values for one or more constants, and to use this information to perform an algorithm to determine a current temperature, and/or a series of temperatures over time, for the housing 19 and/or exterior surface(s) of housing 19 of IMD 14 based on the measured temperature(s) provided by temperature sensors 39 of IMD 14.

Memory 52 may be configured to store instructions for communication with and/or control of one or more temperature sensors 39 of IMD 14. In various examples, memory 52 stores information related to determining the temperature of the housing 19 and/or exterior surface(s) of housing 19 of IMD 14 based on temperatures sensed by one or more temperature sensors, such as temperature sensors 39, located within IMD 14. For example, memory 52 may store one or more formulas, as further described below, that may be used to determine the temperature of the housing 19 and/or exterior surface(s) of housing 19 based on temperature(s) sensed by the temperature sensors 39. Memory 52 may store values for one or more determined constants used by these formulas. Memory 52 may store instructions that, when executed by processing circuitry such as processing circuitry 50, performs an algorithm, including using the formulas, to determine a current temperature, or a series of temperatures over time, for the housing 19 and/or exterior surface(s) of housing 19 of IMD 14 during a charging session and/or for some time after a charging session performed on IMD 14. In some examples, memory 52 may store instructions that, when executed by processing circuitry such as processing circuitry 50, perform an algorithm, including using one or more formulas, to determine a value to be assigned to one or more of the constants used in the algorithm used to determine the temperature(s) associated with the housing 19 and/or exterior surface(s) of housing 19 of IMD 14 during a charging session and/or for some time after a charging session performed on IMD 14.

User interface 54 may include a button or keypad, lights, a speaker for voice commands, a display, such as a liquid crystal (LCD), light-emitting diode (LED), or cathode ray tube (CRT). In some examples, the display may be a touch screen. As discussed in this disclosure, processing circuitry 50 may present and receive information relating to the charging of rechargeable power source 40 via user interface 54. For example, user interface 54 may indicate when charging is occurring, quality of the alignment between coils 40 and 48, the selected power level, current charge level of rechargeable power source 40, duration of the current recharge session, anticipated remaining time of the charging session, sensed temperatures, or any other information. Processing circuitry 50 may receive some of the information displayed on user interface 54 from IMD 14 in some examples. In some examples, user interface 54 may provide an indication to the user regarding the quality of alignment between coils 40, depicted in FIG. 2 and coil 48, based on the charge current to the battery.

User interface 54 may also receive user input via user interface 54. The input may be, for example, in the form of pressing a button on a keypad or selecting an icon from a touch screen. The input may request starting or stopping a recharge session, a desired level of charging, or one or more statistics related to charging rechargeable power source 40 (e.g., the cumulative thermal dose). User input may also include inputs related to temperature thresholds for the IMD that may be used to regulate for example a maximum housing/surface temperature the patient is willing to experience during a charging session of the IMD. The inputs related to threshold values may be store in memory 52, and/or transmitted through telemetry module 56 to IMD 14 for storage in a memory, such as memory 32, located within IMD 14. In this manner, user interface 54 may allow the user to view information related to the charging of rechargeable power source 40 and/or receive charging commands, and to provide inputs related to the charging process. In various examples, user interface 54 as shown and described with respect to FIG. 1 is arranged to perform and to provide the features and/or functions ascribed to user interface 54 as illustrated and described with respect to FIG. 3.

External charging device 22 also includes components to transmit power to recharge rechargeable power source 40 associated with IMD 14. As shown in FIG. 3, external charging device 22 includes primary coil 48 and charging module 58 coupled to power source 60. Charging module 58 may be configured to generate an electrical current in primary coil 48 from electrical energy stored in or provided by power source 60. Although primary coil 48 is illustrated as a simple loop in FIG. 3, primary coil 48 may include multiple turns of wire. Charging module 58 may generate the electrical current according to a power level selected by processing circuitry 50 based on the sensed and/or determined temperature or temperatures received from IMD 14 and/or a temperature sensor within external charging device 22. As described herein, processing circuitry 50 may select a "high" power level, a "low" power level, or a variety of different power levels to control the rate of recharge in rechargeable power source 40 and the temperature of IMD 14. In some examples, processing circuitry 50 may control charging module 58 based on a power level selected by processing circuitry 30 of IMD 14. The determined temperature of the housing 19 and/or exterior surface(s) of housing 19 of IMD 14 used as feedback for control of the recharge power level may be derived from a temperature sensed by a temperature sensor within IMD 14. Although processing circuitry 50 may control the power level used for charging rechargeable power source 40, charging module 58 may include processing circuitry including one or more processors configured to partially or fully control the power level based on the determined temperatures.

Primary coil 48 may include a coil of wire, e.g., having multiple turns, or other devices capable of inductive coupling with a secondary coil 40 disposed within patient 12. Primary coil 48 may include a winding of wire configured such that an electrical current generated within primary coil 48 can produce a magnetic field configured to induce an electrical current within secondary coil 40 depicted in FIG. 2. The induced electrical current may then be used to recharge rechargeable power source 40. In this manner, the electrical current may be induced in secondary coil 40 associated with rechargeable power source 40. The coupling efficiency between secondary coil 40 and primary coil 48 of external charging device 22 may be dependent upon the alignment of the two coils. Generally, the coupling efficiency increases when the two coils share a common axis and are in close proximity to each other. User interface 54 of external charging device 22 may provide one or more audible tones or visual indications of the alignment.

Charging module 58 may include one or more circuits that generate an electrical signal, and an electrical current, within primary coil 48. Charging module 58 may generate an alternating current of specified amplitude and frequency in some examples. In other examples, charging module 58 may generate a direct current. In any case, charging module 58 may be capable of generating electrical signals, and subsequent magnetic fields, to transmit various levels of power to IMD 14. In this manner, charging module 58 may be configured to charge rechargeable power source 40 of IMD 14 with the selected power level. Processing circuitry 50 may calculate $P_{TANK}$, which is the power sent to primary coil 48 and may include the inductance and capacitance between the power generation circuitry of charging module 58 and primary coil 48.

The power level that charging module 58 selects for charging may be used to vary one or more parameters of the electrical signal generated for coil 48. For example, the selected power level may specify wattage, electrical current of primary coil 48 or secondary coil 40, current amplitude, voltage amplitude, pulse rate, pulse width, a cycling rate, or a duty cycle that determines when the primary coil is driven, or any other parameter that may be used to modulate the power transmitted from coil 48. In this manner, each power level may include a specific parameter set that specifies the signal for each power level. Changing from one power level to another power level (e.g., a "high" power level to a lower power level) may include adjusting one or more parameters. For instance, at a "high" power level, the primary coil may be substantially continuously driven, whereas at a lower power level, the primary coil may be intermittently driven such that periodically the coil is not driven for a predetermined time to control heat generation. The parameters of each power level may be selected based on hardware characteristics of external charging device 22 and/or IMD 14.

Power source 60 may deliver operating power to the components of external charging device 22. Power source 60 may also deliver the operating power to charging module 58 to drive primary coil 48 during the charging process. Power source 60 may include a battery and a power generation circuit to produce the operating power. In some examples, a battery of power source 60 may be rechargeable to allow extended portable operation. In other examples, power source 60 may draw power from a wired voltage source such as a consumer or commercial power outlet.

External charging device 22 may include one or more temperature sensors shown as temperature sensor 59 (e.g., similar to temperature sensor 39 of IMD 14) for sensing the temperature of a portion of the device. For example, temperature sensor 59 may be disposed within charging head 26 and oriented to sense the temperature of the housing of charging head 26. In another example, temperature sensor 59 may be disposed within charging head 26 and oriented to sense the temperature of charging module 58 and/or coil 48. In other examples, external charging device 22 may include multiple temperature sensors 59 each oriented to any of these portions of device to manage the temperature of the device during charging sessions.

Telemetry module 56 supports wireless communication between IMD 14 and external charging device 22 under the control of processing circuitry 50. Telemetry module 56 may also be configured to communicate with another computing device via wireless communication techniques, or direct communication through a wired connection, such as external computing device 25 depicted in FIG. 1. In some examples, telemetry module 56 may be substantially similar to telemetry module 36 of IMD 14 described herein, providing wireless communication via an RF or proximal inductive medium. In some examples, telemetry module 56 may include an antenna 57, which may take on a variety of forms, such as an internal or external antenna. Although telemetry modules 56 and 36 may each include dedicated antennas for communications between these devices, telemetry modules 56 and 36 may instead, or additionally, be configured to utilize inductive coupling from coils 40 and 48 to transfer data.

Examples of local wireless communication techniques that may be employed to facilitate communication between external charging device 22 and IMD 14 include radio frequency and/or inductive communication according to any of a variety of standard or proprietary telemetry protocols, or according to other telemetry protocols such as the IEEE 802.11x or Bluetooth specification sets. In this manner, other external devices may be capable of communicating with external charging device 22 without needing to establish a secure wireless connection. As described herein, telemetry module 56 may be configured to receive a signal or data representative of a sensed temperature from IMD 14 or a determined temperature of the housing 19 and/or exterior surface(s) of housing 19 of the IMD based on the sensed temperature. The determined temperature may be determined using an algorithm, including use of formula(s) as further described below, based on measuring the temperature of the internal portion(s) of the IMD, such as circuitry mounted to a circuit board located within IMD 14. In some examples, multiple temperature readings by IMD 14 may be averaged or otherwise used to produce a single temperature value that is transmitted to external charging device 22. The sensed and/or determined temperature may be sampled and/or transmitted by IMD 14 (and received by external charging device 22) at different rates, e.g., on the order of microseconds, milliseconds, seconds, minutes, or even hours. Processing circuitry 50 may then use the received temperature information to control charging of rechargeable power source 40 (e.g., control the charging level used to recharge power source 40).

Figure 4A:
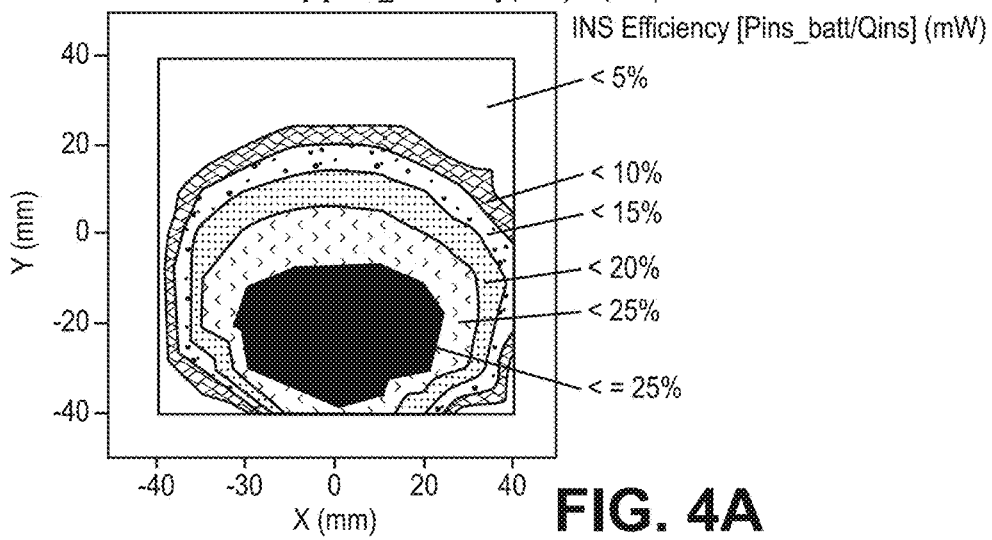
FIGS. 4A-4D are conceptual diagrams illustrating changes in IMD efficiency based on relative location of the primary coil and secondary coil.
Figure 4B:
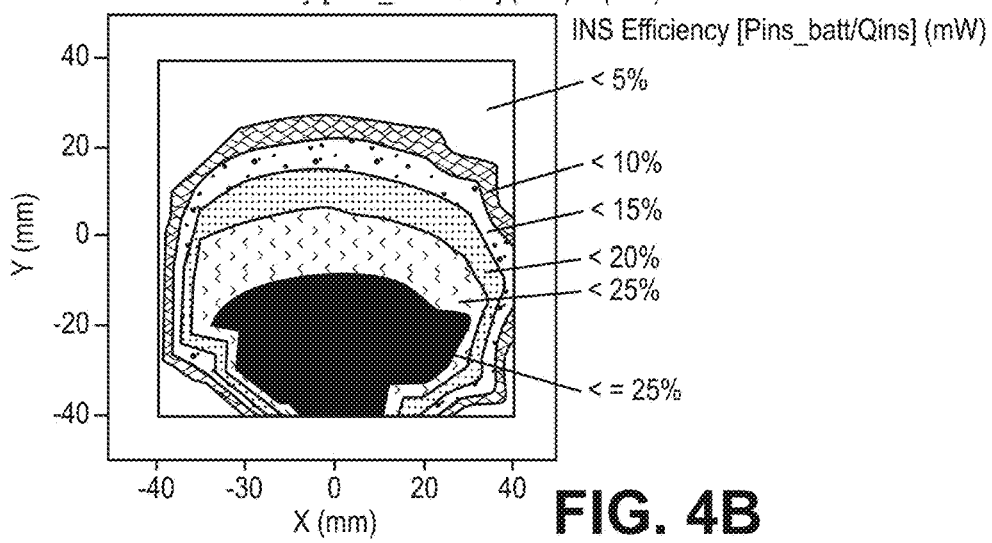
Figure 4C:
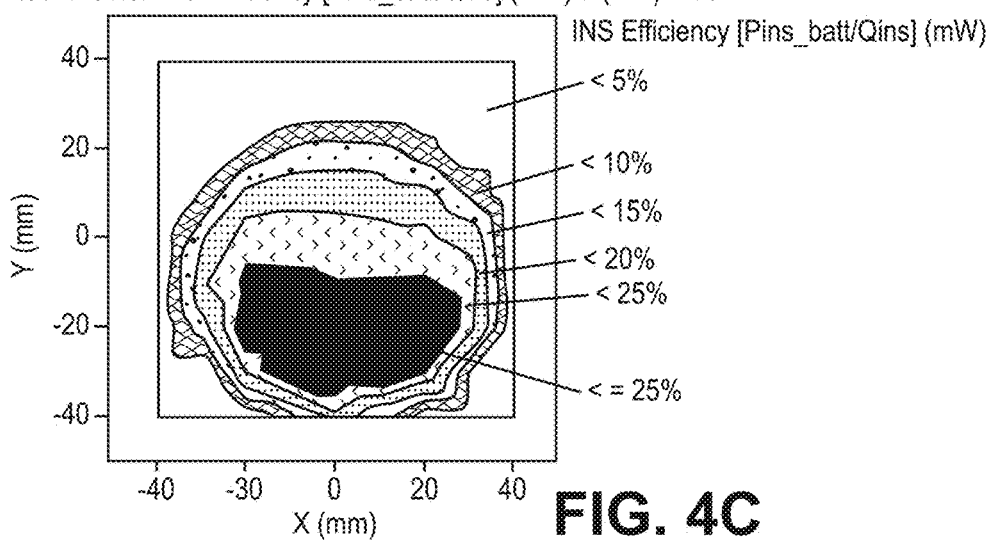

FIGS. 4A-4C are conceptual diagrams illustrating changes in IMD efficiency based on relative location of the primary coil and secondary coil. FIGS. 4A-4C depict contour plots at different separation distances for an example primary coil of a power transmitting unit and secondary coil of a power receiving unit. FIG. 4A illustrates an X-axis and Y-axis of a power receiving device and the changes in IMD efficiency, as the primary coil moves relative to the power receiving device at approximately 10 mm separation. As described above in relation to FIG. 1, IMD efficiency may be defined as (Pimd_batt/$Q_{IMD}$) or (Pimd_batt/Pimd). The center area shows a region in which IMD efficiency is greater than 25%, centered on approximately (0, −20) in the example of FIG. 4A, which may be considered a concentric position, as noted above in relation to FIG. 1. The power transfer efficiency may decrease as the primary coil moves to other regions. Similarly, though not shown in FIGS. 4A-4C, the charge time may increase as the primary coil moves away from the central area. A charge time contour plot may have a similar shape as the efficiency plot shown in FIG. 4A, with the lowest charge times, and lowest heat buildup in the device and surrounding tissue, near regions with the highest IMD efficiency. As noted above in relation to FIG. 1, the term "implantable medical device efficiency" is term used for convenience in this disclosure. The efficiency plots of FIGS. 4A-4C may apply to any power receiving unit, such as a mobile device, mobile phone, remote sensor and so on.

FIG. 4B depicts a contour plot that illustrates changes in IMD efficiency as the primary coil moves relative to the power receiving device at approximately 20 mm separation. Similarly, FIG. 4C depicts a contour plot that illustrates changes in IMD efficiency as the primary coil moves relative to the power receiving device at approximately 30 mm separation. The contour plots change somewhat as the separation distance changes.

Figure 4D:
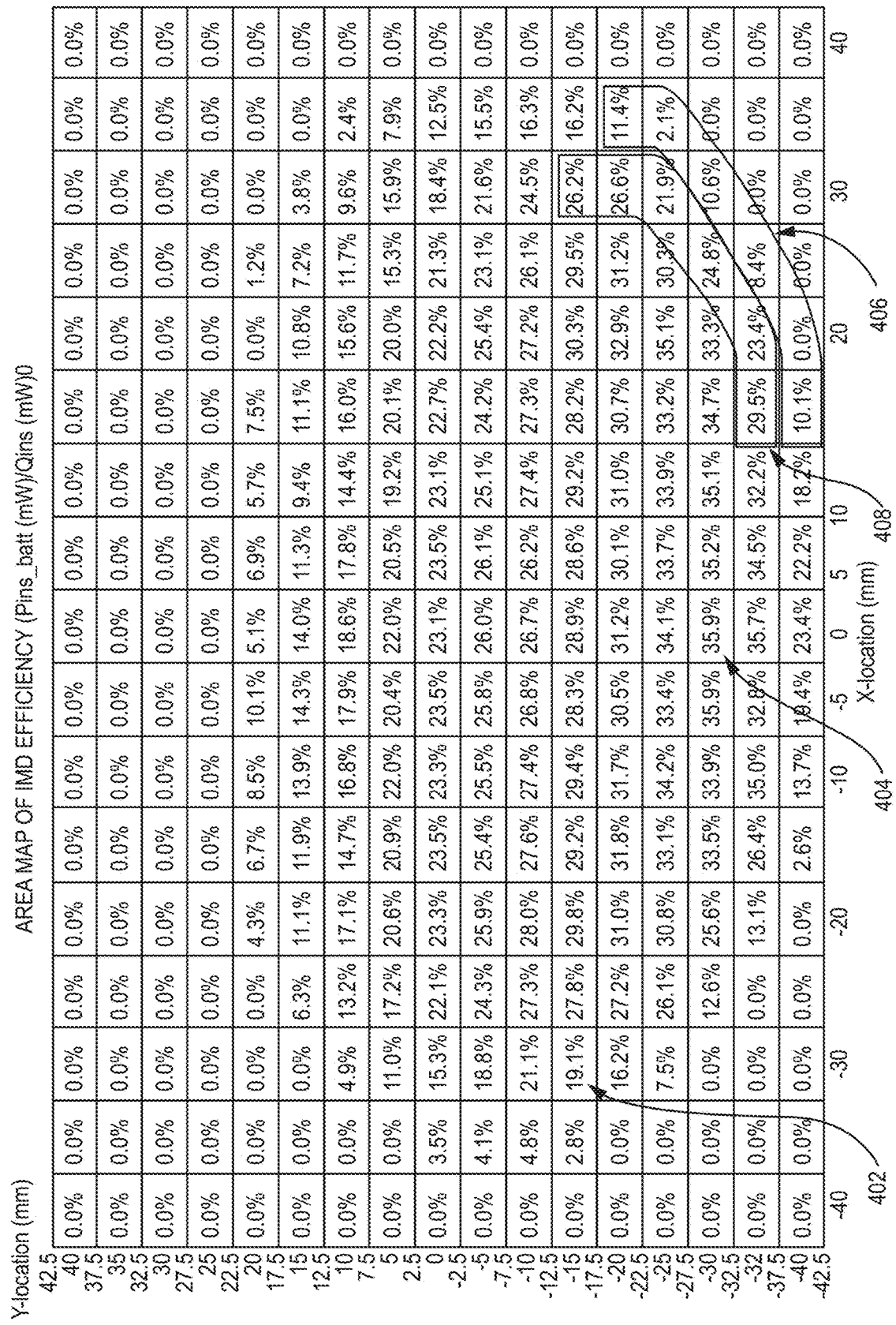

FIG. 4D is a conceptual diagram illustrating an example efficiency map by relative location of the power transmitting unit and the power receiving unit. Areas with the same color indicate zones with approximately equivalent power transfer efficiency, e.g., 402, 404, 406 and 408. In some examples, other measurable factors may more accurately determine the relative location. For example, using an additional factor, such as $Q_{PRIM}$, in an array, e.g., a 3D look up table, along with IMD efficiency may determine an adjustment factor that may more accurately reflect the actual power transfer efficiency. In other examples, a third, fourth or more additional factors may result in a multi-dimensional look-up table, or a multi-dimensional relationship, which the processing circuitry of system 10, described above in relation to FIG. 1, may use to determine the adjustment factor.

In other examples, the additional factor may divide the equivalent zones into smaller zones. For example, the processing circuitry may limit the circle of values indicated by 402 and 408 to just the region indicated by 408 based on the additional factor, such as when $Q_{PRIM}$ is in a first range, use zone 408 and when $Q_{PRIM}$ is outside the first range, use a different zone, within the circle indicated by 402.

In some examples, the feedback to the user at the user interface, e.g., user interface 54 described above in relation to FIG. 3, may include coupling feedback. The coupling feedback displayed by the user interface may spatially map to where the system is delivering more charge current. In this manner the system may provide an indication of the relative location of the primary and secondary coils that may give consistent charge current, consistent energy delivery and consistent charge times.

Figure 5A:
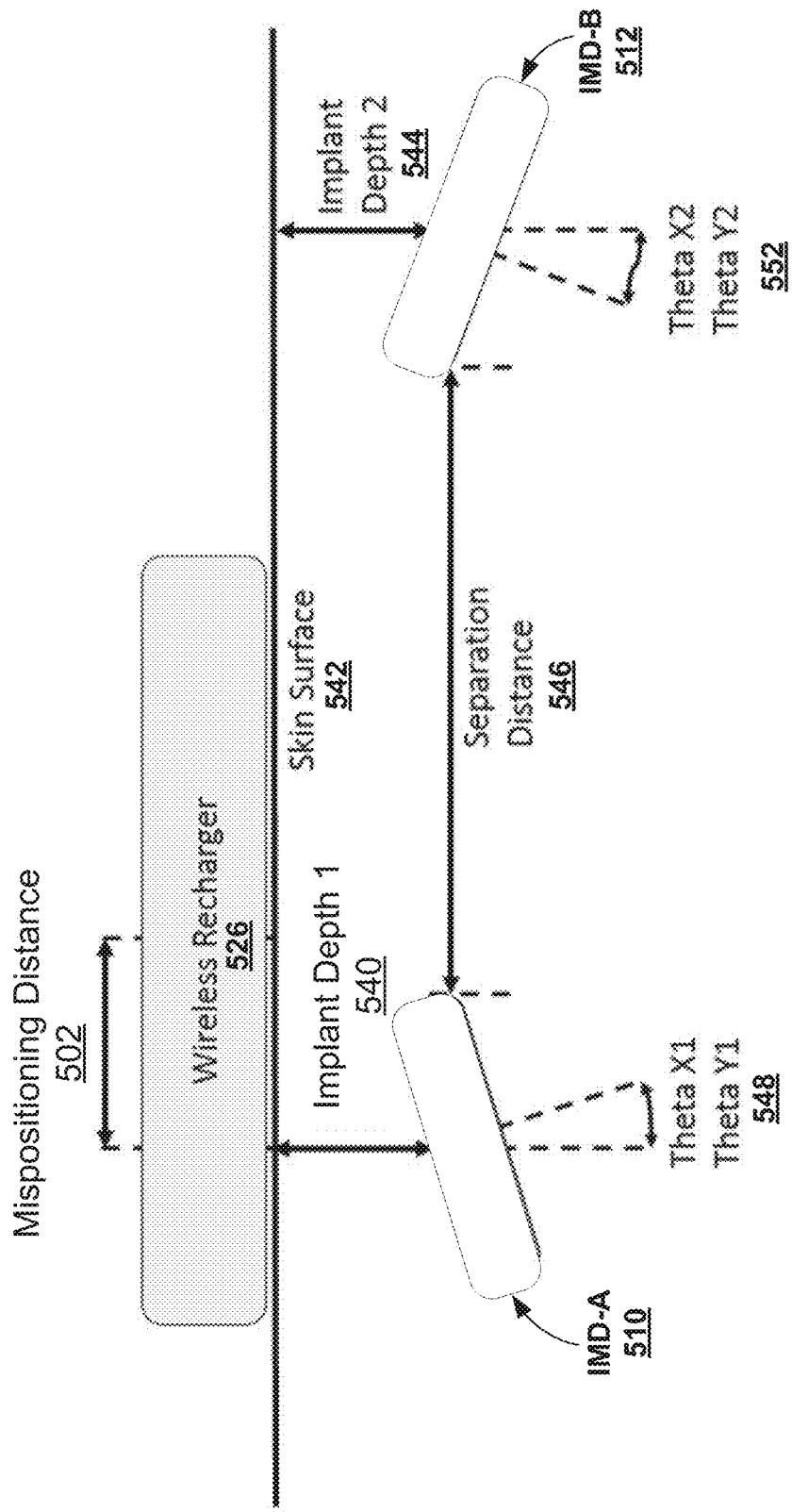
FIG. 5A is a conceptual diagram illustrating example relative positions of a power transmitting unit and a power receiving unit during power transfer.
Figure 5C:
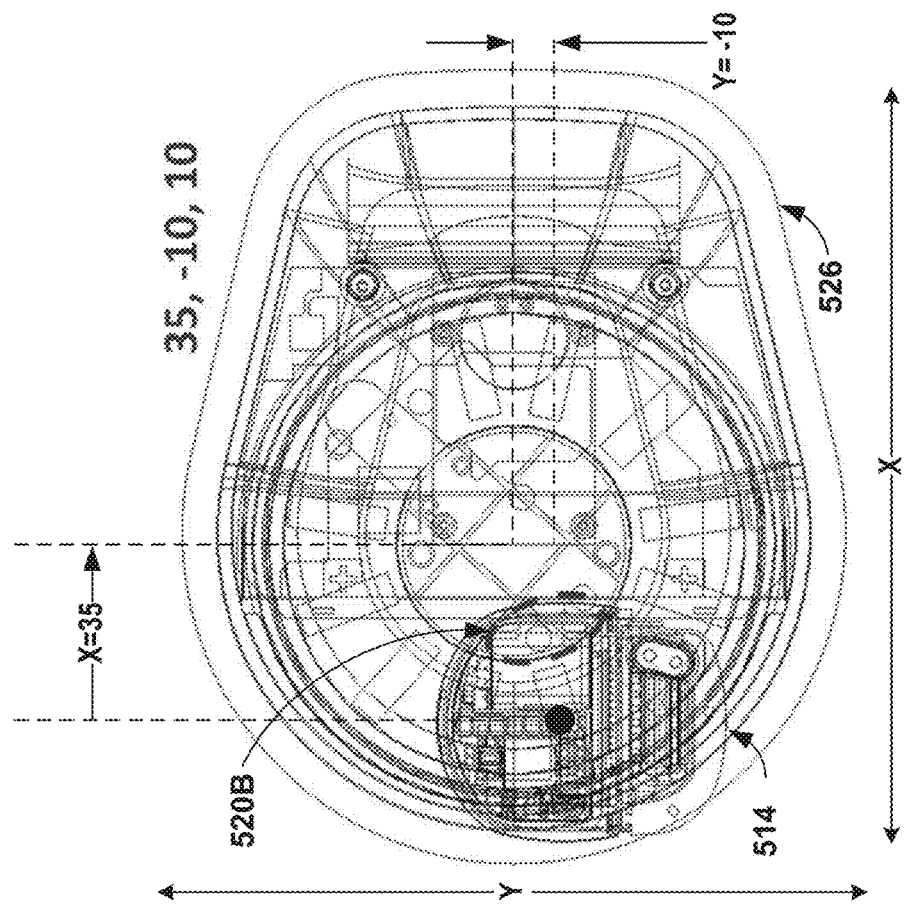
FIGS. 5B and 5C are conceptual diagrams illustrating example relative position changes between power transmitting coil and power receiving coil.
Figure 5B:
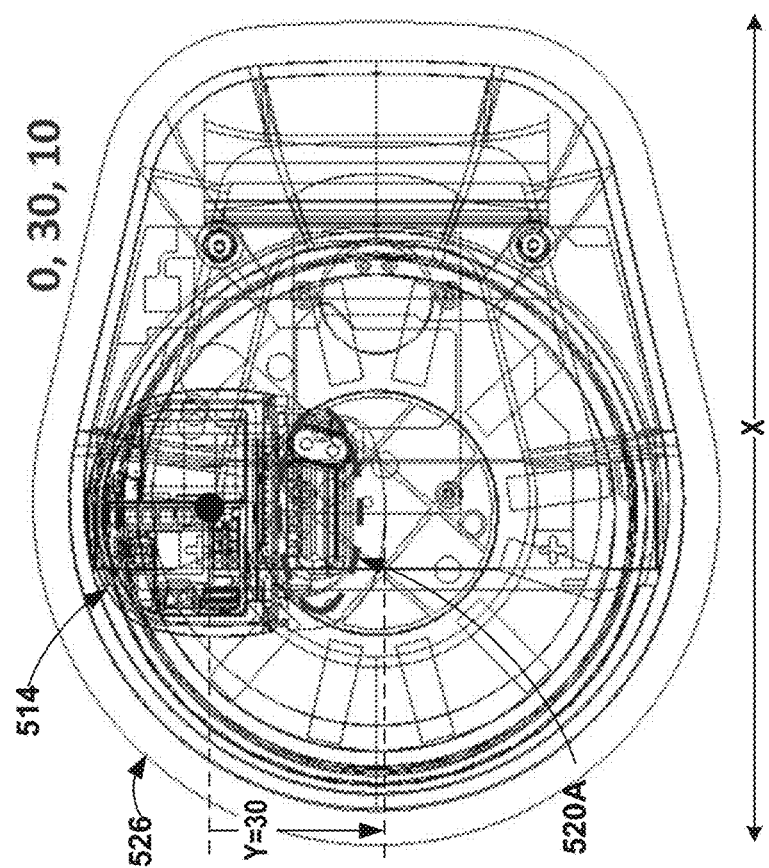

FIGS. 5A and 5B are conceptual diagrams illustrating relative positioning of the power transmitting unit and the power receiving unit. FIG. 5A illustrates wireless recharger 526 at skin surface 542 positioned to recharge either of IMD A 510 or ID B 512. Wireless recharger 526 is an example of charging head 26 described above in relation to FIG. 3. As described above in relation to FIGS. 1 and 3, in some examples, wireless recharger 526 may include a power source, charging module, processing circuitry and a primary coil, such as charging device 22. In other examples, wireless recharger 526 may include fewer components, e.g., only a primary coil and coil housing, or a primary coil along with a charging module, temperature sensor, heat sink device and other components.

Wireless recharge 526 may be offset in the Z-direction by implant depth 1 540 from IMD A 510, which may correspond to the separation distances described above in relation to FIGS. 4A-4C. Wireless recharger 526 may be offset from IMD A 510 in the X-direction and/or Y-direction by mispositioning distance 502. As described above in relation to FIGS. 1-4D, changes in relative position between wireless recharger 526 and IMD A 510 may affect charging efficiency, charge times and heat generated by the power transfer process, caused for example by device heating or tissue heating.

In addition to offset in the X, Y and Z direction, differences in the relative angle, e.g., theta X1/theta Y1 548, between wireless recharger 526 and IMD 510 is another component of the relative position and may also impact charging efficiency. In some examples, processing circuitry, e.g., 50, may cause user interface 54, to output an indication of relative position, as described above in relation to FIGS. 1-3. The indication on the user interface may allow a user to adjust the relative position of wireless recharger 526 to a more efficient location for power transfer.

In some examples, the processing circuitry controlling wireless recharger 526 may multiply the heat limits for IMD 14 in different power transfer modes by an adjustment factor. The AF may be configured as a function of the power transfer efficiency. In other words, processing circuitry for wireless recharger 526 may measure power transfer efficiency, such as IMD efficiency, to determine whether the relative position of wireless recharger 526 and the secondary coil of IMD A 510 may be in a less desirable relative position. The processing circuitry may calculate a new limit, such as using one of the techniques described above based on the measured efficiency and may then adjust power transmitted by wireless recharger 526 based on the newly calculated limit.

In the example of FIG. 5A, IMD B 512 is located at implant depth 2 544 and separated from IND A 510 by separation distance 546. IMD B 512 may also be angled, e.g., relative to skin surface 542 by angle theta X2/theta Y2 552. In some examples, separation distance 546 may be close enough such that IMD B 512 may receive at least some power transferred from wireless recharger 526, while wireless recharger 526 delivers power to IMD A 510. In other examples, a user may reposition wireless recharger 526 to transfer power to IMD B 512.

As described above in relation to FIG. 2, IMD A 510, and/or IMD B 512, may include one or more temperature sensors, such as temperature sensor(s) 39 depicted in FIG. 2. Temperature sensors may be configured to determine the temperature of any of the internal portions of IMD A 510, the housing and/or exterior surface(s) of the housing. In some examples, one of the temperature sensors may be near the center of IMD A 510, or on the housing at the center of the secondary coil of IMD A 510. When another sensor measures a temperature hotter than this central sensor, e.g., the measured temperature exceeds a threshold amount higher than the central sensor, IMD A 510 may signal wireless recharger 526 to change the power output, for example, to charge slower.

In other examples, processing circuitry, e.g., of the power transmitting unit, wireless recharger 526, or processing circuitry of power receiving unit, IMD A 510, may calculate the approximate amount of heat within IMD A 510, ($Q_{IMD}$), such as according to the equations as described above in relation to FIG. 1:

$$Q_{IMD} = P_{TANK} - Q_{PRIM} - Pimd\_batt$$

At the same time, a 2nd order dynamic transfer function to derive temperature output from calculated heat input, $Q_{IMD}$, may keep track of how much the temperature of IMD A 510 may be rising or falling. The 2nd order dynamic transfer function may predict the temperature of IMD A 510, for example based on:

$$Tins(t) = F(IMD\ Efficiency, Q_{IMD}, Tins(t-1))$$

In other examples, for systems with temperature sensors, the function for surface temperature of the housing of IMD A 510 may be based on the additional temperature sensor inputs:

$$Tins(t) = F(IMD\_efficiency, Tsense1, Tsense2, Q_{IMD}, Tins(t-1))$$

Then, the processing circuitry, e.g., of the power transmitting unit and/or power receiving unit 554 may execute a proportional-integrated-derivative (PID) algorithm to control the maximum temperature on the surface contacting portion of the power receiving unit 554.

As described above in relation to FIG. 1, a variety of system metrics may be available to wireless recharger 526, from computations of power and heat by processing circuitry (not shown in in FIG. 5A) that control wireless recharger 526, as well as and the metrics communicated to wireless recharger 526 from IMD A 510, and/or IMD B 512. Some examples of system metrics may include battery current (Iimd_batt) measured by IMD A 510, for fixed power levels or speeds, system power transfer efficiency (Pimd_batt/Ptank), IMD Efficiency e.g., (Pimd_batt/$Q_{IMD}$) or (Pimd_batt/Pimd).

As described above in relation to FIGS. 1-4D, IMD efficiency may be a good indicator of when the primary coil of wireless recharger 526 is concentric with the secondary coil of IMD A 510. A concentric relative location may be a relative position with a high IMD efficiency and a low overall transient thermal response, defined as an increase in temperature for the same calculated heat input ($Q_{IMD}$). In some examples, as described above in relation to FIGS. 4A-4C, positions in which the primary coil is near (0, −20) in X and Y, may charge faster. Therefore, there may exist an exponential relationship between the IMD efficiency and the overall thermal dose in units of CEM43.

In other examples, the system power transfer efficiency (Pimd_batt/Ptank) may be more skewed towards the geometrical center of the IMD A 510, e.g., near (0, 0) in X and Y. In some relative positions of the primary coil and secondary coil, both the IMD efficiency and the system power transfer efficiency metrics may be lower compared to other relative positions. For example, for an implantable medical device that includes a header, the metrics may be lower when the primary coil is positioned over the header of the device, which may lead to decreased power transfer efficiency and a less desirable thermal profile (e.g., a less desirable increase in temp for the same calculated heat input). Furthermore, as described above in relation to FIG. 1, at less efficient relative positions the time to charge may be longer so the overall thermal dose may also be less desirable.

Other techniques of determining the temperature on the surface of the IMD A 510, may have been based on a first order low pass filter or transfer function from the hybrid. The techniques of this disclosure may provide advantages and improve on the other techniques by extend the utility of the other techniques. In other words, the techniques of this disclosure, that include making a second order dynamic transfer function adapt to the changing relative position of wireless recharger 526 and the IMD A 510. In other words, processing circuitry of the system, which may include any of processing circuitry controlling wireless recharger 326, processing circuitry of an external computing device (not shown in FIG. 5A), and/or processing circuitry of IMD A 510, may detect the relative position of the primary and secondary coils, based on one or more metrics available to the system. The processing circuitry may change the behavior of the system based on the one or more metrics, e.g., energy transfer efficiency based on system efficiency, IMD efficiency and so on. In some examples, the IMD efficiency may provide advantages over other metrics, because IMD efficiency may be insensitive, and therefore useable, across the different power transfer modes, where power transfer modes may correlate to charging rates and each mode may have a separate heat limit. In some examples, the processing circuitry may use an adjustment factor, as described above in relation to FIG. 1, which is a monotonically decreasing function for the IMD heat limit that decreases as the system metric becomes less desirable.

The fact that the thermal dynamic transfer function may change as a function of primary and secondary coil relative position may be an additional input that can be added to temperature sensing controlled and/or heat controlled rechargeable systems. Adjusting the power output based on changes in power transfer efficiency may increase the recharge speed and make the system more accurate and therefore safer for patients.

FIGS. 5B and 5C are conceptual diagrams illustrating heat distribution changes as the relative position between power transmitting coil and power receiving coil changes. Wireless recharger 526 in FIGS. 5B and 5C is an example of wireless recharger 526 described above in relation to FIG. 5A and has the same functions and characteristics. IMD 514 in FIGS. 5B and 5C is an example of a power receiving unit, such as IMD 14 described above in relation to FIGS. 1 and 2, and IMD A 510 and IMD B 512 described above in relation to FIG. 5A and may have the same or similar functions and characteristics as IMD 14, IMD A 510 and IMD B 512.

FIGS. 5B and 5C depict a top-down view, similar to the side view illustrated by FIG. 5A. In addition to a relative X, Y and Z position, IMD 514 may be angled relative to wireless recharger 526, as described above in FIG. 5A for angles theta X1/theta Y1 548 and theta X2/theta Y2 552. Wireless recharger 526 and IMD 514 may be separated by one or more layers of material. In some examples, wireless recharger 526 may be located in the seat of an automobile, a recliner, a mattress, or other piece of furniture and separated from the power receiving unit of IMD 514 by layers of leather, padding, cloth, or other material. In other examples, IMD 514 may be implanted in a patient, and separated from wireless recharger 526 by layers of skin, muscle, fatty tissue, blood vessels, bone and so on.

In the example of FIG. 5B, IMD 514 and wireless recharger 526 are in a first relative position, e.g., (0, 30 mm, 10 mm). For this power receiving unit, IMD 514 with this wireless recharger 526, the zone indicated by 520A may reach a higher temperature than other areas of IMD 514. In the example of FIG. 5C, IMD 514 and wireless recharger 526 are in a second relative position, e.g., (35 mm, −10 mm, 10 mm). In the second relative position, the higher temperature zone may move to the area indicated by 520B. In some examples, some of the charging energy being transferred from wireless recharger 526, instead of coupling to the secondary coil of IMD 514 the energy may cause increased eddy currents in one or more components of IMD 514 or may cause direct heating of tissue, in the example of an implantable device. In some examples, the duration of the recharge time, which may be impacted by the energy transfer efficiency, may also contribute to heating certain portions of IMD 514.

Figure 5D:
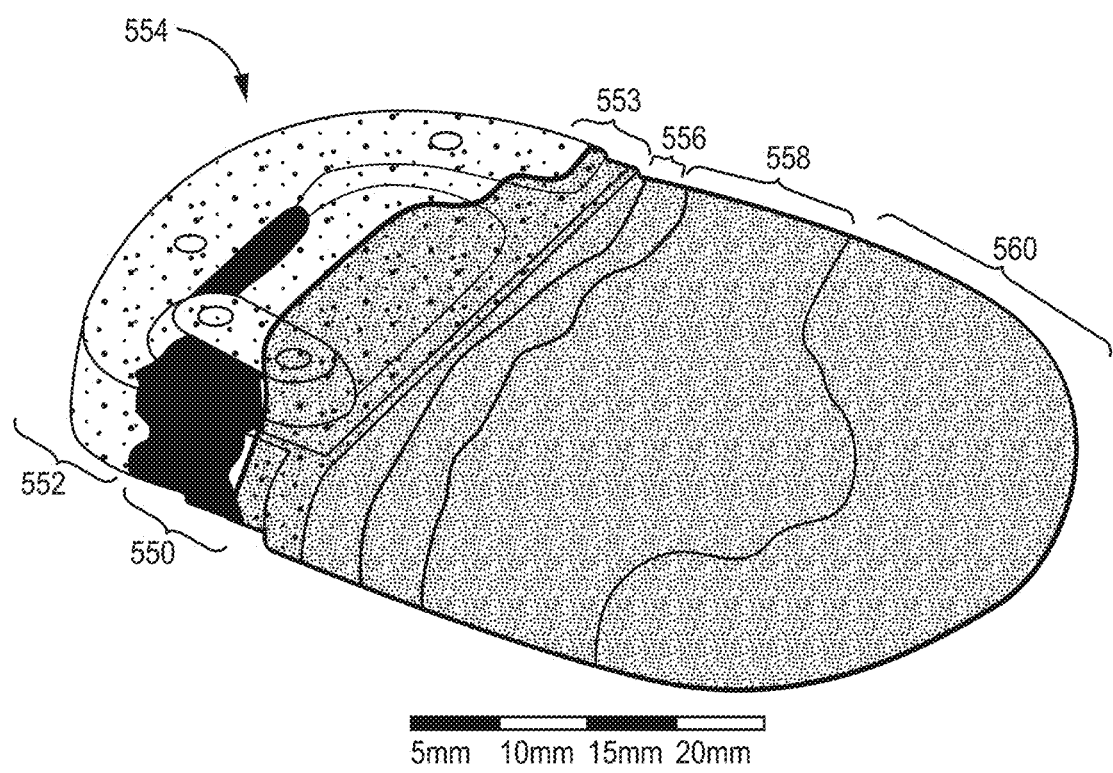
FIG. 5D is a conceptual diagram illustrating an example heat distribution on an example power receiving unit during power transfer.

FIG. 5D is a conceptual diagram illustrating an example heat distribution on an example power receiving unit during power transfer. Power receiving unit 554 is an example of the power receiving units described above in relation to FIGS. 1, 2, 4A-4D and 5A-5C, e.g., IMD 14, IMD A 510, IMD B 512 and IMD 514. In the example, of FIG. 5D, power receiving unit 554 may be oriented relative to a power transmitting unit (not shown in FIG. 5D) such that a region of highest temperature is region 550. The region with the lowest temperature is region 560. The regions closer to region 550 may register a higher temperature compared to region 560. For example, regions 558, 556 and 554 may increase in temperature compared to region 560, with region 553 at a higher temperature than regions 556 and 558. Changing the relative position of power receiving unit 554 compared to the power transmitting unit may change the relative temperatures of the regions.

Figure 5E:
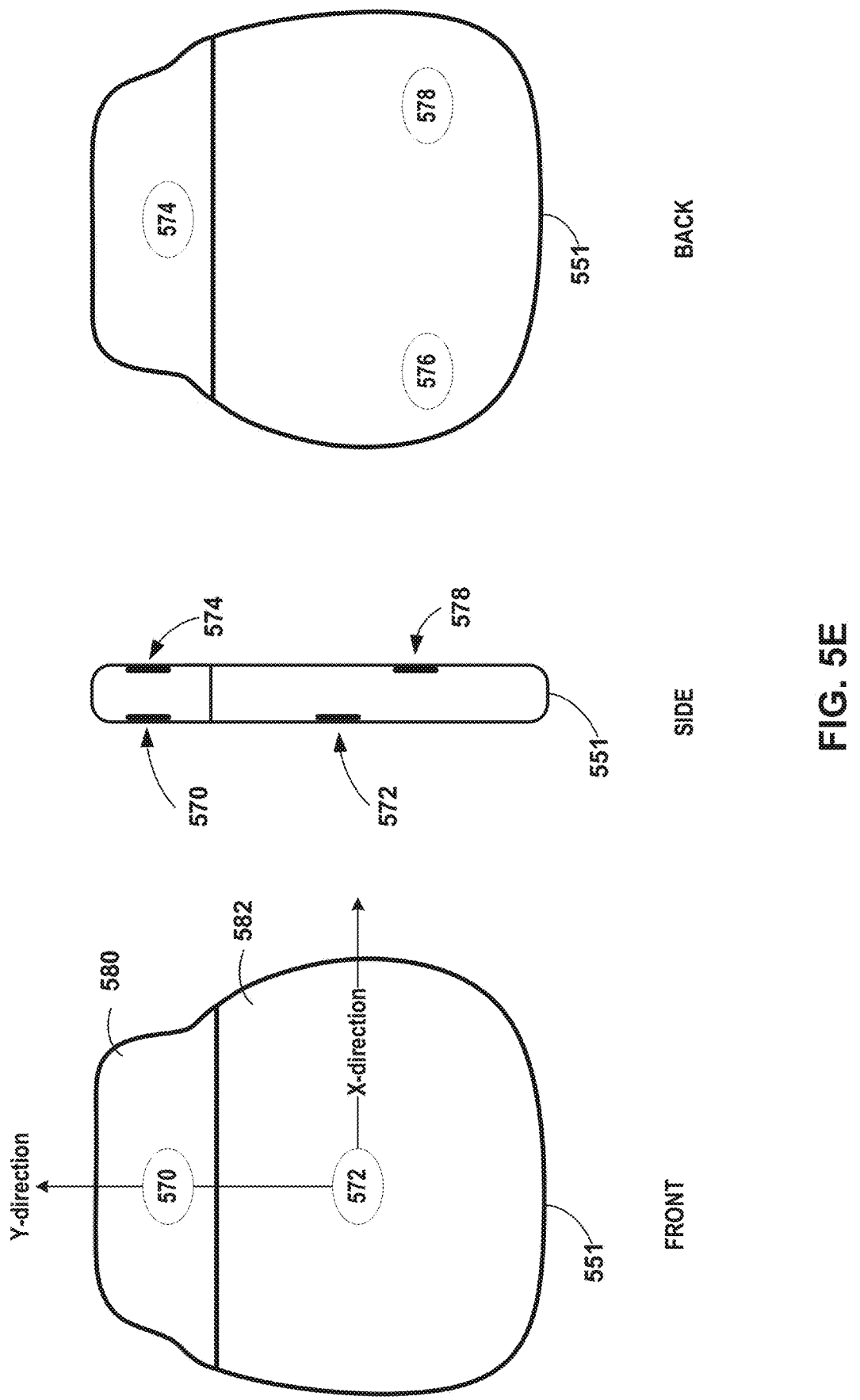
FIG. 5E is a conceptual diagram illustrating example temperature sensors for an IMD of this disclosure.

FIG. 5E is a conceptual diagram illustrating example temperature sensors for an IMD of this disclosure. The example of FIG. 5E depicts temperature sensors located at various locations on the housing and the header of IMD 551, which is an example of IMD 14 described above in relation to FIGS. 1 and 2. In some examples, the temperatures sensors in FIG. 5E may be temporary and used for testing IMD temperature in the lab. In other examples, IMD 551 may include more or fewer temperature sensors, and placed in different locations than the locations shown in FIG. 5E. As described above in relation to FIGS. 1, 2, and 5A, the adaptive recharge algorithm of this disclosure may include multiple temperature sensor inputs to the algorithm in addition to the IMD efficiency. Processing circuitry of this disclosure may control the recharge power based on measured temperatures and/or temperature gradients across the device as well as the power transfer efficiency, calculations of the amount of heat, and other system metrics.

As described above in relation to FIGS. 1 and 4D, the adaptive recharge algorithm may use a look-up table, in some examples, in the form of a multi-dimensional array. Temperature vector inputs to the adaptive algorithm may add second, third, or higher order dimensions to the look up table for control set points in the adaptive recharge algorithm.

As one example, the temperature difference may increase with increasing X or Y relative displacement to a point, then the temperature difference may eventually return back to no difference, when the relative position of the charging coil and IMD coil is a large enough distance. In contrast, IMD efficiency may start high, when the coils are nearly concentric. The IMD efficiency may decrease with increasing distance. So, the combination of these two inputs, temperature deltas and IMD efficiency, may provide the system a proxy for relative position. The relative position may be defined using radial or cartesian coordinates and may depend on how many temperature sensors located on the IMD. In some examples, the combined information including the temperature gradients may increase the recharge area, e.g., the size of the area in which the relative position of the system including the power transmitting coil and power receiving coil still effectively transfer power. In some examples, including temperature sensors may improve usability by allowing higher heats at positions which an adaptive recharge algorithm that only considered IMD efficiency may not be able distinguish one position from another, as described above in relation to FIG. 4D.

In the example of FIG. 5E, sensors 570 and 574 are located on the front side and back side, respectively of header 580 of IMD 551. Sensor 572 is approximately centered on the front side of housing 582 of IMD 551. In the example of FIG. 5E, sensor 572 marks the origin of the X-direction and Y-direction. Sensors 576 and 578 are separated in the X-direction on the back side of housing 582. Though shown adjacent to housing 582, in the example of FIG. 5E, in other examples one or more temperature sensors may also be located within housing 582, and at some distance from the housing, e.g., mounted as an element on a circuit board. To simplify the description, a temperature gradient in the Y direction may be defined, in the example of FIG. 5E as the difference between a first temperature (T1) measured at sensor 570 and a second temperature (T2) measured at sensor 572. A temperature gradient in the X-direction may be defined, in the example of FIG. 5E as a difference between a third temperature (T3) measured at sensor 578 and a fourth temperature (T4) measured at sensor 576. In other examples, not shown in FIG. 5E, the adaptive recharge algorithm may include other temperature gradients between other temperature sensors.

In some examples, the adaptive recharge algorithm may estimate the maximum temperature on IMD 551 based on temperature gradients, efficiency, or some combination of different system metrics as inputs to the algorithm. Processing circuitry executing the adaptive recharge algorithm may vary the temperature control limit according to a look up table based on different vectors including T1-T2 (Y direction), T4-T3 (X-direction), IMD efficiency (similar to a radius), and possibly other metrics like Qprim, as described above in relation to FIGS. 1 and 4D. Other dimensions may add to the look-up table, such as additional temperature gradients. In other words, the system may generate a representative temperature from a plurality of temperature sensors and use the representative temperature in the adaptive recharge algorithm as described herein.

In some examples, the estimated maximum temperature may be a function of the different temperature readings received by the processing circuitry from the various temperature sensors. In this disclosure, the control function may be based on whatever point in space on IMD 551 is the hottest, e.g., the "estimated maximum temperature." In some examples, the temperature sensors may be mounted in a position on IMD 551 that is not the hottest. The processing circuitry may estimate the hot spot temperature, e.g., estimated maximum temperature, somewhere different than directly near a temperature sensor. For example, processing circuitry may calculate the maximum temperature according to:

$$T_{max} = k_1|(T_1-T_2)| + \text{Avg}(T_1, T_2)$$

or $$T_{max} = \begin{cases} k_1|(T_1+T_2)| + \text{Avg}(T_1, T_2) \\ k_2|(T_3+T_4)| + \text{Avg}(T_3, T_4) \end{cases}$$

In other examples the estimated maximum temperature may include conditional logic, such as:

IF T1 > T2
   $T_{max12} = k_{1a}(T_1 - T_2) + Avg(T_1, T_2)$
Else
   $T_{max12} = k_{1b}(T_2 - T_1) + Avg(T_1, T_2)$
End In some examples, the adaptive recharge algorithm of this disclosure may use the calculated temperatures to adjust a setpoint, such as a PID setpoint, as described above in relation to FIGS. 1 and 5A, according to the below look-up table:

Sample Look-up table with temperature gradient

| IMD Efficiency | T1-T2 → 0.1-0.2 | 0.2-0.5 | 0.6-0.7 | 0.8-1.0 |
|---|---|---|---|---|
| 0-5% | 41 | 41 | 41 | 41 |
| 6-10% | 41 | 41 | 41 | 41 |
| 11-15% | 41.5 | 41.5 | 41.5 | 41 |
| 16-20% | 42 | 42 | 42 | 41 |
| 21-25% | 43 | 43 | 42.5 | 41.5 |
| 26-30% | 43.5 | 43.5 | 42.5 | 42 |
| >30% | 44 | 43.5 | 43 | 42 |

In some examples, the multi-dimensional look up table may have higher temperatures in certain relative locations, set to prevent any harm to the patient and harm to the IMD, which may be caused by heat dissipated from an inefficient relative position. At the same time, the processing circuitry may perform calculations to maximize the recharge area and performance.

Figure 5G:
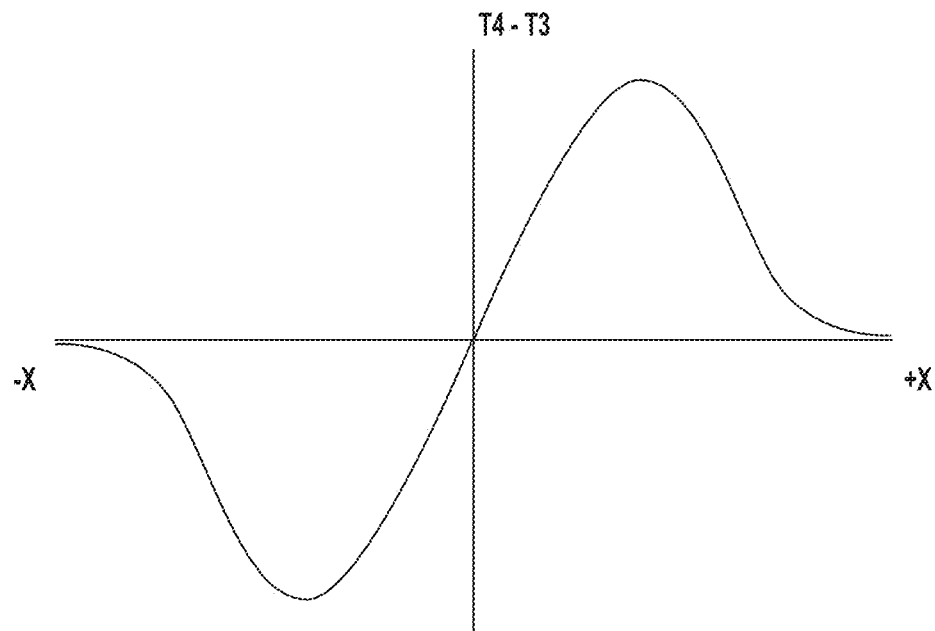
FIG. 5G is a graph illustrating an example temperature gradient in the X direction as described above in FIG. 5E.
Figure 5H:
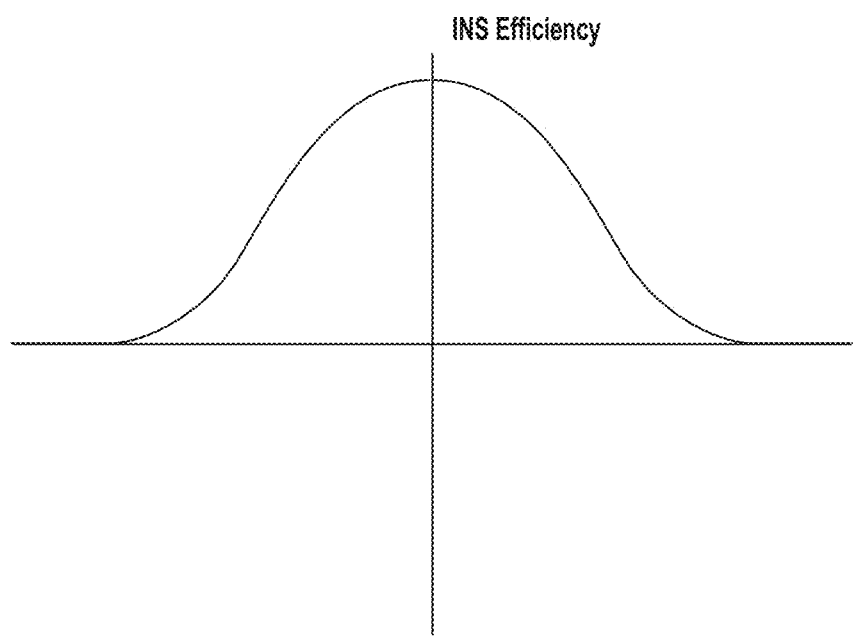
FIG. 5H is a graph illustrating an example of IMD efficiency as the relative position of the power transmitting coil and power receiving coil change.

FIG. 5F is a graph illustrating an example temperature gradient in the Y direction (T1-T2) as described above in FIG. 5E. FIG. 5G is a graph illustrating an example temperature gradient in the X direction (T4-T3) as described above in FIG. 5E. FIG. 5H is a graph illustrating an example of IMD efficiency as the relative position of the power transmitting coil and power receiving coil change.

Figure 6:
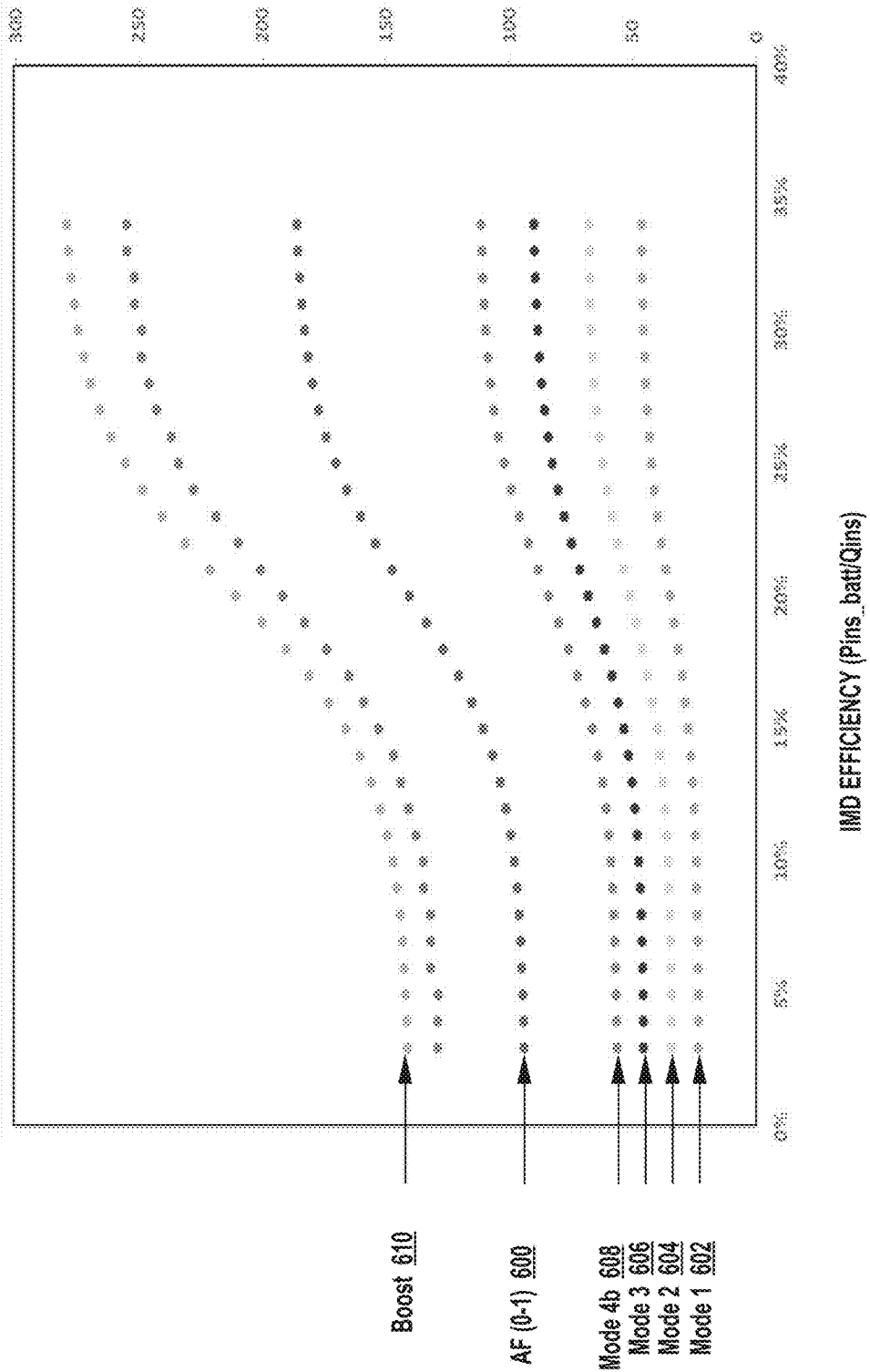
FIG. 6 is a graph illustrating an example output of an example adjustment factor look-up table.

FIG. 6 is a graph illustrating an example output of an example adjustment factor look-up table. The table below includes one example look-up table for the adjustment factor and FIG. 6 depicts a sample graph of the adjustment factor as IMD efficiency changes. In other examples, e.g., for different types of power transmitting units and power receiving units, the values may differ from those in FIG. 6.

$Q_{IMD}$ Limit Adjustment Factor

| IMD Efficiency (Pimd_batt/ $Q_{IMD}$) Threshold (%) | Adjustment Factor *256 |
|---|---|
| <3% | 128 |
| 3% | 129 |
| 4% | 129 |
| 5% | 129 |
| 6% | 132 |
| 7% | 132 |
| 8% | 132 |
| 9% | 135 |
| 10% | 135 |
| 11% | 138 |
| 12% | 141 |
| 13% | 144 |
| 14% | 147 |
| 15% | 153 |

-continued $Q_{IMD}$ Limit Adjustment Factor

| IMD Efficiency (Pimd_batt/ $Q_{IMD}$) Threshold (%) | Adjustment Factor *256 |
|---|---|
| 16% | 159 |
| 17% | 165 |
| 18% | 174 |
| 19% | 183 |
| 20% | 192 |
| 21% | 201 |
| 22% | 210 |
| 23% | 219 |
| 24% | 228 |
| 25% | 234 |
| 26% | 237 |
| 27% | 243 |
| 28% | 246 |
| 29% | 249 |
| 30% | 249 |
| 31% | 252 |
| 32% | 252 |
| 33% | 255 |
| 34% | 255 |
| >34% | 256 |

As described above in relation to FIG. 1, the recharging system, e.g., system 10 may measure efficiency, such as IMD efficiency, to determine whether the relative position of the primary coil and secondary coil may be in a less desirable relative position. Processing circuitry of the recharging system may calculate a new heat limit for the power receiving unit, such as a heat limit between the minimum and maximum allowable heat limit. System 10 may then adjust power transmitted based on the newly calculated limit using the adjustment factor from the table above. As described above in relation to FIG. 1, the AF may be configured as a function of the IMD efficiency and the range of possible values on AF may be set as from 0 to 1. In the example above, the adjustment factor is multiplied by $256=2^8$.

FIG. 6, depicts an example for the adjustment factor for the different modes, e.g., mode 1 602, mode 2, 604, mode 3 606, mode 4b 708 and boost mode 610. FIG. 6 also include a plot of the adjustment factor 600. Each mode may include heat limits for the IMD, e.g., $Q_{IMD}$, heat limits for the primary coil $Q_{PRIM}$, battery current limit IIMD_BATT, and so on. In other examples, the values may vary based on, for example, a specific wireless recharger, a power receiving unit, size of the primary coil and secondary coil, whether the power receiving unit is an implantable medical device or a different type of device, such as a hearing aid, mobile computing device, rechargeable sensor and so on.

Figure 7:
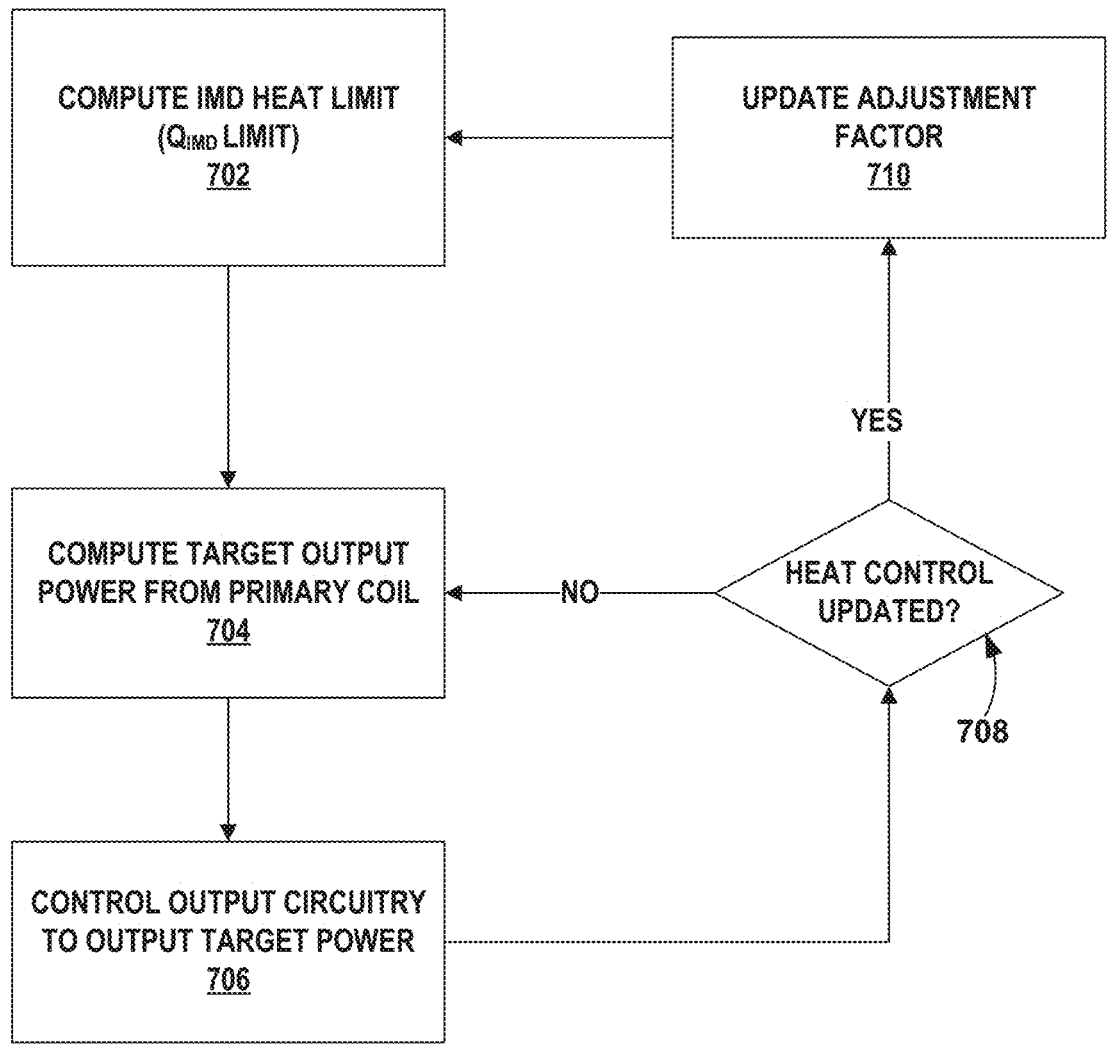
FIG. 7 is a flowchart illustrating an example operation of the system of this disclosure.

FIG. 7 is a flowchart illustrating an example operation of the system of this disclosure. The blocks of FIG. 7 will be described based on FIGS. 1-3, unless otherwise noted. A wireless charging system may include a power transmitting unit and a power receiving unit, such as an implantable medical device, IMD 10. In some examples, processing circuitry, such as processing circuitry 50, may execute instructions stored at, for example, memory 52 to execute the blocks of FIG. 7. In other examples, processing circuitry of other components of system 10, such as processing circuitry of charging system 22, processing circuitry of external computing device 25, and/or processing circuitry of IMD 14 may execute one or more blocks of FIG. 7, or steps within blocks of FIG. 7.

Based on the power transfer mode, the processing circuitry may determine the IMD heat limit, $Q_{IMD}$ limit, (702).

The IMD heat limit may be stored in a memory, such as memory 52 and be based on the power transfer mode. For example, a wireless power transfer system using the values from FIG. 6 above in the boost mode (mode 4a), may determine the IMD heat limit is less than or equal to 1500 mW.

The processing circuitry executing the recharging algorithm of this disclosure may compute target output power from the primary coil, $P_{TANK}$ (704). In some examples, processing circuitry 50 of charging device 22, depicted in FIG. 3, may compute the target output power. In other examples, processing circuitry 30 of IMD 14, depicted in FIG. 2, or processing circuitry of external computing device 25, depicted in FIG. 1, may compute the target output power based on communication with charging device 22.

The processing circuitry may further control the output circuitry, e.g., charging module 58, to output the target power from primary coil 48 (706). As described above in relation to FIG. 1, the processing circuitry may compute IMD_Efficiency during closed loop power transfer according to the equation:

$$IMD\_efficiency = Pimd\_batt / Q_{IMD}.$$

As noted above in relation to FIG. 1, Qins and $Q_{IMD}$ as well as INS_efficiency and IMD_efficiency may be used interchangeably in this disclosure.

IMD 14 may measure the power, Pimd_batt sent to the battery or other power source, from recharge module 38. In some examples, processing circuitry of IMD 14 may output via telemetry module 36, the measured power, e.g., Pimd_batt. In some examples, processing circuitry may measure Iimd_batt and compute Pimd_batt based on the voltage of power source 40. If the Pimd_batt is zero, then IMD_efficiency may be returned as zero. Processing circuitry of system 10 may calculate the heat, $Q_{IMD}$, and compare the calculated $Q_{IMD}$ to the heat limit based on the below equation, as described above in relation to FIG. 1:

$$Q_{IMD} = P_{TANK} - Q_{PRIM} - Pimd\_batt$$

In some examples, the recharging algorithm may include timers, and other limits. Based on exceeding one or more limits, or other factors in the recharging algorithm, the processing circuitry may change to a different power transfer mode, or IMD_efficiency may change, e.g., based on a change in relative position between the primary coil 26 and secondary coil 16, depicted in FIG. 1, which may drive an update to the heat control limit (708).

In some examples, the recharging algorithm may stay in the same power transfer mode and/or the IMD_efficiency stays approximately the same and therefore make no change to the heat control (NO branch of 708). For example, though the relative position of primary coil 26 and secondary coil 16 may move, the IMD_efficiency may remain approximately equivalent, such as within region 404 or 406 described above in relation to FIG. 4D.

In other examples, the processing circuitry may change to a different power transfer mode, or IMD_efficiency may change, which may drive a change in heat control (YES branch of 708). For example, primary coil 26 may move from region 404 to 402 as shown in FIG. 4D, or between regions of higher IMD_efficiency to a region of lower IMD_efficiency, as shown in FIGS. 4A-4C.

The processing circuitry may update the adjustment factor (710) based on a table similar to adjustment factor above or based on one or more other linear or non-linear relationships described above in relation to FIG. 1. The processing circuitry of the recharger may adjust the current $Q_{IMD}$ limit for the current power transfer mode based on the adjustment factor (702). In some examples, it may be desirable to have the adjustment factor adjusted at a slower rate, e.g., less often, than the algorithm controlling the $Q_{IMD}$ limit to avoid oscillations in the control algorithm. For example, the adjustment factor may be updated at a rate that is 5 to 10 times slower than the main control algorithm.

In one or more examples, the functions described above may be implemented in hardware, software, firmware, or any combination thereof. For example, the various components of FIGS. 2 and 3, such as processing circuitry 30 and processing circuitry 50 may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

The term "non-transitory" may indicate that the storage medium is not embodied in a carrier wave or a propagated signal. In certain examples, a non-transitory storage medium may store data that can, over time, change (e.g., in RAM or cache).

By way of example, and not limitation, such computer-readable storage media, may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer readable media. In some examples, an article of manufacture may include one or more computer-readable storage media.

Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Combinations of the above should also be included within the scope of computer-readable media.

Instructions may be executed by one or more processors, such as one or more DSPs, general purpose microprocessors, ASICs, FPGAs, or other equivalent integrated or discrete logic circuitry. Accordingly, the term "processor," as used herein, may refer to any of the foregoing structure or any other structure suitable for implementation of the techniques described herein. Also, the techniques could be fully implemented in one or more circuits or logic elements.

The techniques of this disclosure may be implemented in a wide variety of devices or apparatuses, including, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

The devices, systems and techniques may also be shown in the following examples.

Example 1: A device comprising a power transmitting unit configured to wirelessly transfer electromagnetic energy to a power receiving unit; and processing circuitry configured to: compute a target output power deliverable by the power transmitting unit for a first duration; control the power transmitting unit to output the target output power based in part on a heat limit; calculate an energy transfer efficiency to the power receiving unit; update an adjustment factor based on the calculated energy transfer efficiency; and apply the adjustment factor to the heat limit for a subsequent duration.

Example 2: The device of example 1, wherein the processing circuitry is further configured to: compute an amount of heat received at the power receiving unit based on: the target output power; and an amount of heat lost by a primary coil of the power transmitting unit; and calculate the energy transfer efficiency to the power receiving unit based on the computed amount of heat received by the power receiving unit.

Example 3: The device of any of examples 1 and 2, wherein the processing circuitry is configured to receive an indication of an amount of power delivered to an electrical energy storage device of the power receiving unit.

Example 4: The device of example 3, wherein the processing circuitry is configured to calculate the energy transfer efficiency based on an amount of heat received by the power receiving unit and the amount of power delivered to the electrical energy storage device of the power receiving unit.

Example 5: The device of any of examples 3 and 4, wherein the processing circuitry is configured to calculate the energy transfer efficiency based on an amount of heat received by the power receiving unit and the amount of power delivered to the electrical energy storage device of the power receiving unit.

Example 6: The device of example 5, wherein the processing circuitry is further configured to: control the power transmitting unit to operate in a first power transfer mode; compute an amount of heat received by the power receiving unit; compare the computed amount of heat received by the power receiving unit to the heat limit for the subsequent duration; and determine whether to operate in a first power transfer mode or a second power transfer mode for the subsequent duration based on the comparison.

Example 7: The device of example 6, wherein while operating in the second power transfer mode, the power transmitting unit outputs less electromagnetic energy than while operating in the first power transfer mode.

Example 8: The device of any of examples 5 through 7, wherein the processing circuitry is configured to avoid oscillations in the control algorithm, wherein to avoid oscillations in the control algorithm comprises to update the heat limit more often than updating the adjustment factor.

Example 9: The device of any of examples 1 through 8, further comprising a temperature sensor configured to measure a temperature of a primary coil of the power transmitting unit.

Example 10: The device of any of examples 1 through 9, wherein the processing circuitry is configured to: receive an indication of a first temperature from a first temperature sensor at a first location on the power receiving unit; receive an indication of a second temperature from a second temperature sensor at a second location on the power receiving unit; compare the first temperature to the second temperature; and compute the target output power based on the comparison.

Example 11: The device of any of examples 1 through 10, wherein a relationship between the adjustment factor and the energy transfer efficiency is a non-linear transfer function.

Example 12: The device of any of examples 1 through 11, wherein a relationship between the adjustment factor and the energy transfer efficiency is a monotonic transfer function.

Example 13: The device of any of examples 1 through 12, wherein the processing circuitry determines the adjustment factor based on a look-up table that includes the energy transfer efficiency.

Example 14: A system comprising a power receiving unit; a power transmitting unit configured to wirelessly transfer electromagnetic energy to the power receiving unit; and comprising processing circuitry configured to: compute a target output power deliverable by the power transmitting unit for a first duration; control the power transmitting unit to output the target output power based in part on a heat limit; calculate an energy transfer efficiency to the power receiving unit; and update an adjustment factor based on the calculated energy transfer efficiency; and apply the adjustment factor to the heat limit for a subsequent duration.

Example 15: The system of example 14, wherein the processing circuitry is further configured to: compute an amount of heat received at the power receiving unit based on: the target output power; and an amount of heat lost by a primary coil of the power transmitting unit; and calculate the energy transfer efficiency to the power receiving unit based on the computed amount of heat received by the power receiving unit.

Example 16: The system of any of examples 14 and 15, wherein the processing circuitry is configured to receive, from the power receiving unit, an indication of an amount of power delivered to an electrical energy storage device of the power receiving unit.

Example 17: The system of example 16, wherein the processing circuitry is configured to: receive an indication of an amount of heat received by the power receiving unit; calculate the energy transfer efficiency based on: the amount of heat received by the power receiving unit; and the amount of power delivered to the electrical energy storage device of the power receiving unit.

Example 18: The system of any of examples 15 through 17, wherein the processing circuitry is further configured to: operate the power transmitting unit in a first power transfer mode; compare the computed amount of heat received at the power receiving unit to the heat limit for the subsequent duration; and determine whether to operate in a first power transfer mode or a second power transfer mode for the subsequent duration based on the comparison.

Example 19: The system of example 18, wherein while operating in the second power transfer mode, the power transmitting unit is configured to output less electromagnetic energy than while operating in the first power transfer mode.

Example 20: The system of any of examples 14 through 19, wherein the power receiving unit is an implantable medical device.

Example 21: The system of any of examples 14 through 20, further comprising a temperature sensor.

Example 22: The system of example 21, wherein the temperature sensor is configured to measure a temperature of a primary coil of the power transmitting unit, and wherein the processing circuitry is configured to calculate the energy transfer efficiency based in part on the temperature of the primary coil.

Example 23: The system of any of examples 21 and 22, wherein the temperature sensor is configured to measure a temperature of the power receiving unit, and wherein the processing circuitry is configured to calculate the energy transfer efficiency based in part on the temperature of the primary coil.

Example 24: The system of example 23, wherein the temperature sensor is a first temperature sensor at a first location on the power receiving unit, the system further includes receive an indication of a first temperature from a first temperature sensor at a first location on the power receiving unit; receive an indication of a second temperature from a second temperature sensor at a second location on the power receiving unit; compare the first temperature to the second temperature; and compute the target output power based on the comparison.

Example 25: A method comprising computing, by processing circuitry, a target output power deliverable by a wireless power transmitting unit for a first duration; controlling, by the processing circuitry, circuitry to output the target output power based in part on a heat limit; calculating, by the processing circuitry, an energy transfer efficiency to a power receiving unit; and updating, by the processing circuitry, an adjustment factor based on the calculated energy transfer efficiency applying the adjustment factor to the heat limit for a subsequent duration.

Various examples of the disclosure have been described. These and other examples are within the scope of the following claims.

What is claimed is:

1. A device comprising:
a power transmitting unit configured to wirelessly transfer electromagnetic energy to a power receiving unit; and
processing circuitry configured to:
compute a target output power deliverable by the power transmitting unit for a first duration;
control the power transmitting unit to output the target output power;
receive an indication of a first temperature from a first temperature sensor at a first location of the power receiving unit;
receive an indication of a second temperature from a second temperature sensor at a second location of the power receiving unit;
compare the first temperature to the second temperature; and compute the target output power for a subsequent duration based on the first temperature and the second temperature.

2. The device of claim 1, wherein the processing circuitry is configured to: determine a temperature gradient based on the comparison of the first temperature to the second temperature; and
compute the target output power for the subsequent duration based on the temperature gradient.

3. The device of claim 2,
wherein the power receiving unit comprises a plurality of temperature sensors,
wherein the temperature gradient is a first temperature gradient;
wherein the processing circuitry is further configured to determine two or more temperature gradients;
wherein the processing circuitry is configured to compute the target output power for the subsequent duration based on the two or more temperature gradients.

4. The device of claim 1, wherein the processing circuitry is further configured to:
compute an amount of heat received at the power receiving unit based on:
the target output power; and
an amount of heat lost by a primary coil of the power transmitting unit; and
calculate an energy transfer efficiency to the power receiving unit based on at least the computed amount of heat received by the power receiving unit.

5. The device of claim 1,
wherein the processing circuitry is configured to receive an indication of an amount of power delivered to an electrical energy storage device of the power receiving unit, and wherein the processing circuitry is further configured to calculate an energy transfer efficiency based on an amount of heat received by the power receiving unit and the amount of power delivered to the electrical energy storage device of the power receiving unit.

6. The device of claim 5, wherein the processing circuitry is configured to:
calculate an energy transfer efficiency based at least on an indication received from the power receiving unit; and
execute an adaptive recharge algorithm based on a combination of the calculated energy transfer efficiency and the comparison of the first temperature and the second temperature.

7. The device of claim 5,
wherein a relative position comprises a relative position between the power transmitting unit and the power receiving unit; and
wherein the processing circuitry is configured to distinguish a first relative position from a second relative position based on a combination of the calculated energy transfer efficiency and the comparison of the first temperature and the second temperature.

8. The device of claim 5, further comprising a temperature sensor configured to measure a temperature of a primary coil of the power transmitting unit, wherein the processing circuitry is further configured to execute the adaptive recharge algorithm based at least in part on the temperature of the primary coil.

9. The device of claim 1, wherein the processing circuitry is configured to estimate a third temperature at a third location on the power receiving unit based on the indication of the first temperature and the second temperature.

10. A device comprising:
a user interface;
a power transmitting unit configured to wirelessly transfer electromagnetic energy to a power receiving unit; and
processing circuitry configured to:
calculate a coupling position, wherein the coupling position comprises a relative position between the power transmitting unit and the power receiving unit;

cause the user interface to output an indication of an alignment of the power transmitting unit and the power receiving unit based on the calculated relative position.

11. The device of claim 10, wherein the processing circuitry configured to:
receive an indication of a first temperature from a first temperature sensor at a first location on the power receiving unit;
receive an indication of a second temperature from a second temperature sensor at a second location on the power receiving unit;
compare the first temperature to the second temperature;
calculate the coupling position based on the comparison.

12. The device of claim 10, wherein the processing circuitry is configured to calculate the coupling position based on an energy transfer efficiency.

13. The device of claim 12, wherein the processing circuitry is further configured to:
receive an indication of a first temperature from a first temperature sensor at a first location on the power receiving unit;
receive an indication of a second temperature from a second temperature sensor at a second location on the power receiving unit;
compare the first temperature to the second temperature;
calculate the coupling position based on the energy transfer efficiency and the comparison of the first temperature and the second temperature.

14. The device of claim 13, wherein the processing circuitry is configured to receive an indication of an amount of power delivered to an electrical energy storage device of the power receiving unit.

15. The device of claim 13, wherein the processing circuitry is configured to calculate the energy transfer efficiency based on an amount of heat received by the power receiving unit and the amount of power delivered to the electrical energy storage device of the power receiving unit.

16. The device of claim 13, wherein the processing circuitry is configured to calculate the energy transfer efficiency based on an amount of heat received by the power receiving unit and the amount of power delivered to the electrical energy storage device of the power receiving unit.

17. A method comprising:
computing, by processing circuitry, a target output power deliverable by a wireless power transmitting unit for a first duration;
controlling, by the processing circuitry, circuitry to output the target output power based in part on a heat limit;
receiving an indication of a first temperature from a first temperature sensor at a first location on the power receiving unit;
receiving an indication of a second temperature from a second temperature sensor at a second location on the power receiving unit;
comparing the first temperature to the second temperature;
updating an adjustment factor based on the first temperature and the second temperature; and
applying the adjustment factor to the heat limit for a subsequent duration.

18. The method of claim 17, further comprising:
determining a temperature gradient based on the comparison of the first temperature to the second temperature; and
updating the adjustment factor based on the temperature gradient.

19. The method of claim 17, further comprising:
calculating an energy transfer efficiency based at least on an indication received from the power receiving unit; and
updating the adjustment factor based on the combination of the energy transfer efficiency and the comparison of the first temperature and the second temperature.

20. The method of claim 17,
wherein the power receiving unit comprises a plurality of temperature sensors,
wherein the temperature gradient is a first temperature gradient;
the method further comprising:
determining two or more temperature gradients; and
updating the adjustment factor based on the two or more temperature gradients.

* * * * *